United States Patent [19]
Jandrue, Sr. et al.

[11] Patent Number: 5,244,771
[45] Date of Patent: Sep. 14, 1993

[54] PHOTOGRAPHIC PRODUCTS AND PROCESSES

[75] Inventors: Charles E. Jandrue, Sr., Norwood; Marcis M. Kampe, Brookline; Myron S. Simon, West Newton; David P. Waller, Lexington; David C. Whritenour, Franklin, all of Mass.

[73] Assignee: Polaroid Corporation, Cambridge, Mass.

[21] Appl. No.: 747,807

[22] Filed: Aug. 20, 1991

[51] Int. Cl.$^5$ .......................... G03C 1/84; G03C 5/54
[52] U.S. Cl. ..................................... 430/221; 430/236; 430/227; 430/244; 430/517; 430/449; 430/486
[58] Field of Search ............... 430/221, 517, 944, 236, 430/227, 244, 449, 248

[56] References Cited
U.S. PATENT DOCUMENTS

| | | | |
|---|---|---|---|
| 3,000,833 | 9/1961 | Coleman et al. | 252/300 |
| 3,415,644 | 12/1968 | Land | 430/220 |
| 3,415,645 | 12/1968 | Land | 430/220 |
| 3,415,646 | 12/1968 | Land | 430/220 |
| 3,702,244 | 11/1972 | Bloom et al. | 430/221 |
| 3,702,245 | 11/1972 | Simon et al. | 430/221 |
| 4,615,966 | 10/1986 | Borror et al. | 430/221 |
| 4,886,733 | 12/1989 | Simon | 430/221 |
| 4,891,298 | 1/1990 | Waller | 430/221 |

FOREIGN PATENT DOCUMENTS

| | | |
|---|---|---|
| 0209259 | 1/1987 | European Pat. Off. |
| 61-228986 | 10/1986 | Japan |
| 615112 | 7/1978 | U.S.S.R. |
| 1363870 | 8/1984 | United Kingdom |

OTHER PUBLICATIONS

Chemical Abstract No. 89:148,275b, S. M. Kazakova et al., "Composition for Heat-Sensitive Coating", p. 76, 1978.
D. A. Brown and M. J. S. Dewar, J. Chemical Soc., 1954, pp. 2134-2136.

*Primary Examiner*—Richard L. Schilling
*Attorney, Agent, or Firm*—Carol A. Loeschorn

[57] ABSTRACT

A novel class of bridged indicator dyes is disclosed which possess absorption in the infrared region of the electromagnetic spectrum. These bridged indicator dyes are useful as light-absorbing, pH-sensitive optical filter agents in diffusion transfer photographic processes adapted to be performed in the presence of ambient light and to diffusion transfer products useful in such processes. These indicator dyes will also find utility in titrations and other analytical techniques and products where pH-sensitive indicator dyes are employed and absorption of infrared is useful.

54 Claims, 10 Drawing Sheets

PHOTOGRAPHIC PRODUCTS AND PROCESSES

BACKGROUND OF THE INVENTION

1. Field of the Invention

This invention relates to novel bridged indicator dyes. In another aspect it relates to photography and, more particularly, to photographic processes and products wherein the novel bridged indicator dyes are employed as optical infrared filter agents to protect a selectively exposed photosensitive material from further exposure during processing in ambient light.

2. Description of the Relevant Art

Photographic processes for producing both black-and-white and color images in which development of the light-sensitive photographic material is conducted outside of the camera in the presence of ambient light are now well known. Of particular interest in such photographic processes are diffusion transfer systems wherein the image-receiving layer carrying the transfer image is not separated from the developed photosensitive layer(s) after processing but both components are retained together as a permanent integral laminate, the final image being viewed through a transparent (support) element against a reflective, i.e., white, background. Such systems are described, for example, in U.S. Pat. Nos. 3,415,644, 3,415,645 and 3,415,646 issued Dec. 10, 1968 to Edwin H. Land.

These systems generally employ a light-absorbing material or optical filter agent in the processed film unit together with a layer of a light-reflecting material, preferably titanium dioxide, to protect the selectively exposed silver halide emulsions from post-exposure fogging during development in ambient light. The optical filter agents absorb light from a specific region of the spectrum thereby preventing or at least inhibiting light of that specific region from reaching and exposing the light-sensitive layer. The concentrations of optical filter agent and light-reflecting material required to provide adequate protection of the photosensitive layer(s) will vary with the process being performed and the anticipated conditions, e.g., light intensity, dark time, etc. and may be readily determined for any photographic process by routine experimentation.

In a preferred embodiment, the optical filter agent is a pH-sensitive dye, i.e., a dye possessing spectral absorption characteristics that are reversibly alterable in response to changes in environmental pH and particularly, a pH-sensitive dye having a colored or light-absorbing form above a given alkaline pH and a colorless or non-light-absorbing form below said pH. Such pH-sensitive dyes are frequently referred to as indicator dyes.

Various pH-sensitive dyes have been disclosed as light-absorbing optical filter agents. Examples of such indicator dyes found to be particularly useful for protection in the visible region of the spectrum are the phthaleins, i.e., the phthalide and naphthalide dyes derived from indoles disclosed in U.S. Pat. No. 3,702,244 issued Nov. 7, 1972 to Stanley M. Bloom, Alan L. Borror, Paul S. Huyffer and Paul T. MacGregor, and the phthalide and naphthalide dyes derived from phenols and 1-naphthols disclosed in U.S. Pat. No. 3,702,245 issued Nov. 7, 1972 to Myron S. Simon and David P. Waller. As discussed in the latter patent, phenol and 1-naphthol phthaleins especially useful for photographic processes employing highly alkaline media are those possessing a hydrogen-bonding group, for example, a carboxy group ortho to the p-hydroxy group of the phenol or naphthol radicals. As discussed in these and other patents, the 1-naphthol or phenol phthaleins are generally used in combination with the indole phthaleins where it is desired to provide protection from post-exposure fogging throughout the visible spectrum.

U.S. Pat. No. 4,886,733 issued Dec. 12, 1989 to Myron S. Simon discloses unsubstituted phenanthrol/o-carboxynaphthol phthaleins which provide opacification extending into the far red and near infrared. Substituted phenanthrol/o-carboxynaphthol phthaleins are disclosed in U.S. Pat. No. 4,891,298 issued Jan. 2, 1990 to David P. Waller which also absorb into the far red and near infrared ($\lambda\mathrm{max} \approx 680$ nm) but which possess a broader absorption spectrum and absorb incident radiation more strongly at the longer wavelengths than the unsubstituted phenanthrol/o-carboxynaphthol phthaleins and di-(o-carboxynaphthol) phthaleins. Additionally, they show increased absorption in the blue and green region of the spectrum.

In photographic systems where the silver halide light-sensitive emulsion has been optically sensitized to the longer wavelength infrared region, e.g., systems which electronically expose a spectrally sensitized photosensitive element with infrared radiation emitted from a semiconductor laser or LED, pH-sensitive opacification dyes which will filter out extraneous incident infrared radiation during ambient processing are required.

U.S. Pat. No. 3,000,833, issued Sep. 19, 1961, discloses fluoren-9-ol salts represented by the formula

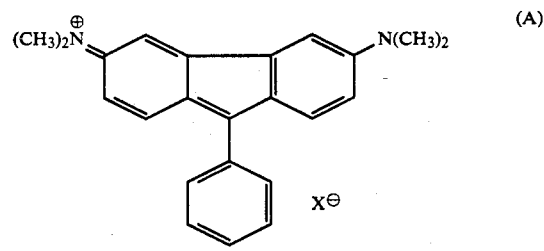

(A)

which absorb more strongly in the near infrared relative to the corresponding basic triphenylmethane dyes represented by the formula

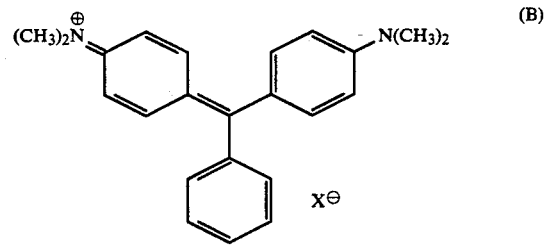

(B)

which absorb more strongly in the visible range. This bathochromic shift (shift to the longer wavelength region) which occurs when the triphenylmethane compound is bridged to make the fluorene derivative is ascribed to the additional C-C bond as discussed in D. A. Brown and M. J. S. Dewar, J. Chemical Soc., 2134 (1954).

European Patent Application Publication No. 209259, published Jan. 1, 1987 and Japanese Patent Kokai No. 61-228986, Laid Open Oct. 13, 1986, disclose bridged phthalide derivatives of the formula

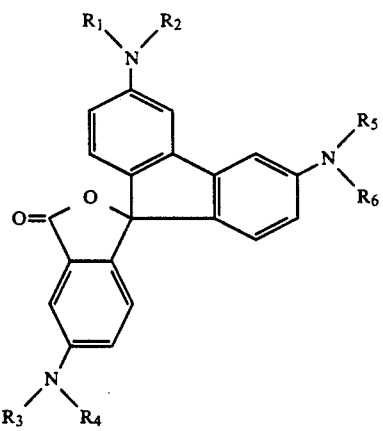

(C)

which react with an electron accepting acidic material upon contact to produce color images which possess a strong absorption in the infrared range of 700-900 nm.

Thus, while many materials are known which absorb in the near infrared, pH-sensitive dyes having a colored or light-absorbing form above a given alkaline pH and a colorless or non-light-absorbing form below said pH and possess a strong absorption in the near infrared region (defined here as the region falling between approximately 700 nm and 1500 nm) are as yet unknown.

SUMMARY OF THE INVENTION

According to the present invention, it has been found that a novel class of bridged indicator dyes derived from certain amino substituted carbocyclic aryl compounds and/or certain hydroxy-substituted carbocyclic aryl compounds exhibit absorption in the 700 to 950 nm near-infrared region while being pH-sensitive, that is, colored at a first alkaline pH value above their respective pKa but become colorless at a second, less alkaline pH value below their respective pKa. By pKa is meant the pH at which about 50% of the dye is present in its light-absorbing form.

It is, therefore, the primary object of the present invention to provide novel bridged indicator dyes.

It is another object of the present invention to provide diffusion transfer photographic products and processes employing as the processing composition, an aqueous alkaline solution of a light-reflecting pigment and a bridged indicator dye as at least one light-absorbing, pH-sensitive optical filter agent.

It is another object of the present invention to provide photographic products and processes of the foregoing type wherein the processing composition additionally includes a light-absorbing, pH-sensitive alkyl substituted phenanthrol/carboxynaphthol phthalein optical filter agent and/or a light-absorbing indole phthalein optical filter agent.

Other objects of this invention will in part be obvious and will in part appear hereinafter.

The invention accordingly comprises the processes involving the several steps and the relation and order of one or more of such steps with respect to each of the others, and the products possessing the features, properties and relation of elements which are exemplified in the following detailed disclosure, and the scope of the application of which will be indicated in the claims.

It will be appreciated that the bridged indicator dyes of this invention will find utility in titrations and other analytical procedures where indicator dyes are employed and absorption of infrared is useful, for example, to measure changes in pH value as reflected by the change in color of the dye from one color to another or from colorless to colored or vice versa and in products which employ on/off infrared radiation. The indicator dyes of the present invention, however, compared to other known indicator dyes, possess absorption in the near infrared which render them particularly useful as optical filter agents in photographic processes wherein the silver halide emulsion is sensitive to the near infrared region of the spectrum.

For a fuller understanding of the nature and objects of the invention, reference should be had to the following detailed description taken in conjunction with the accompanying drawings.

DETAILED DESCRIPTION OF THE INVENTION

Figure 1:
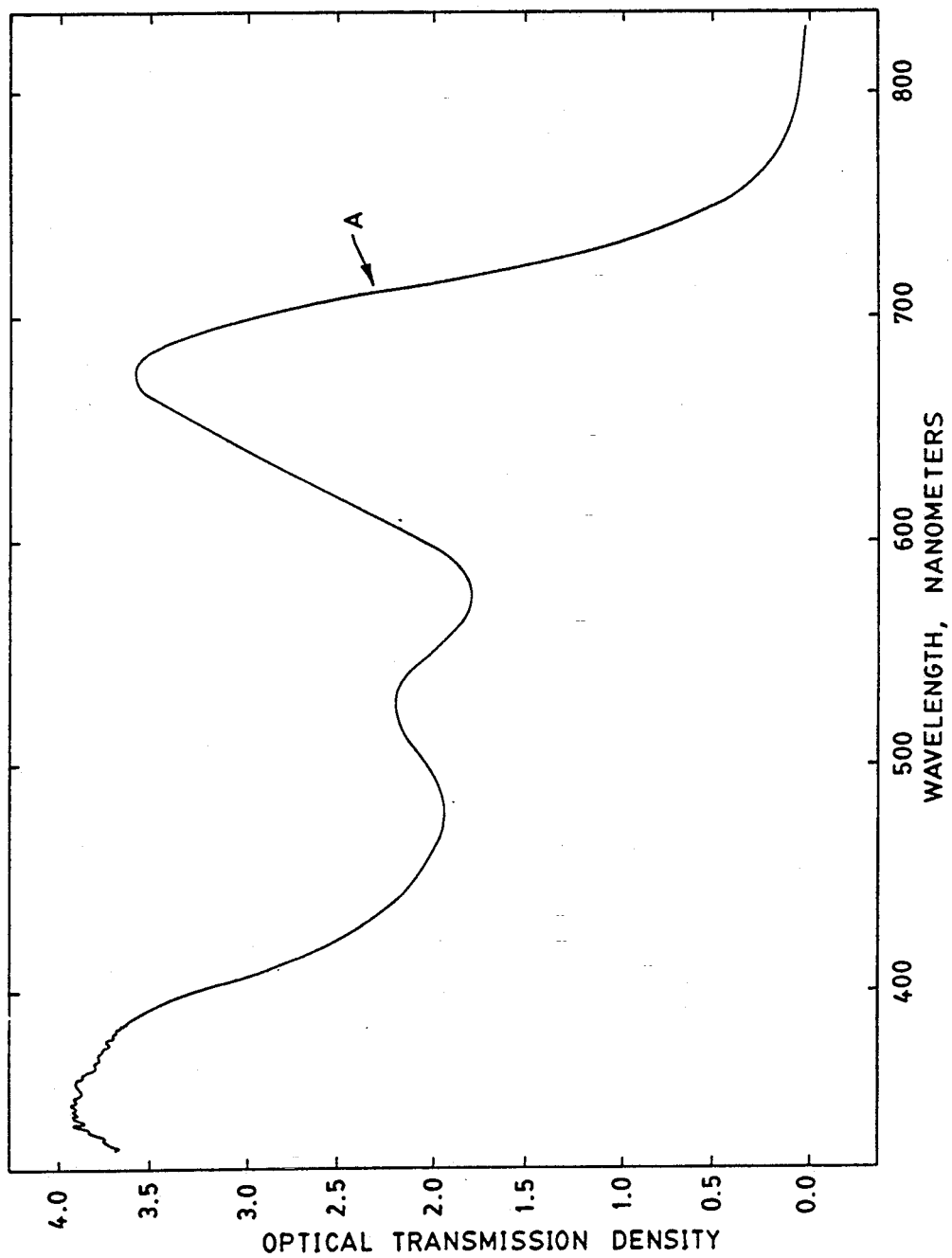
FIG. 1 is a graphic illustration of the spectral absorption characteristics of a mixture of two indicator dyes which absorb in the visible region of the spectrum.
Figure 2:
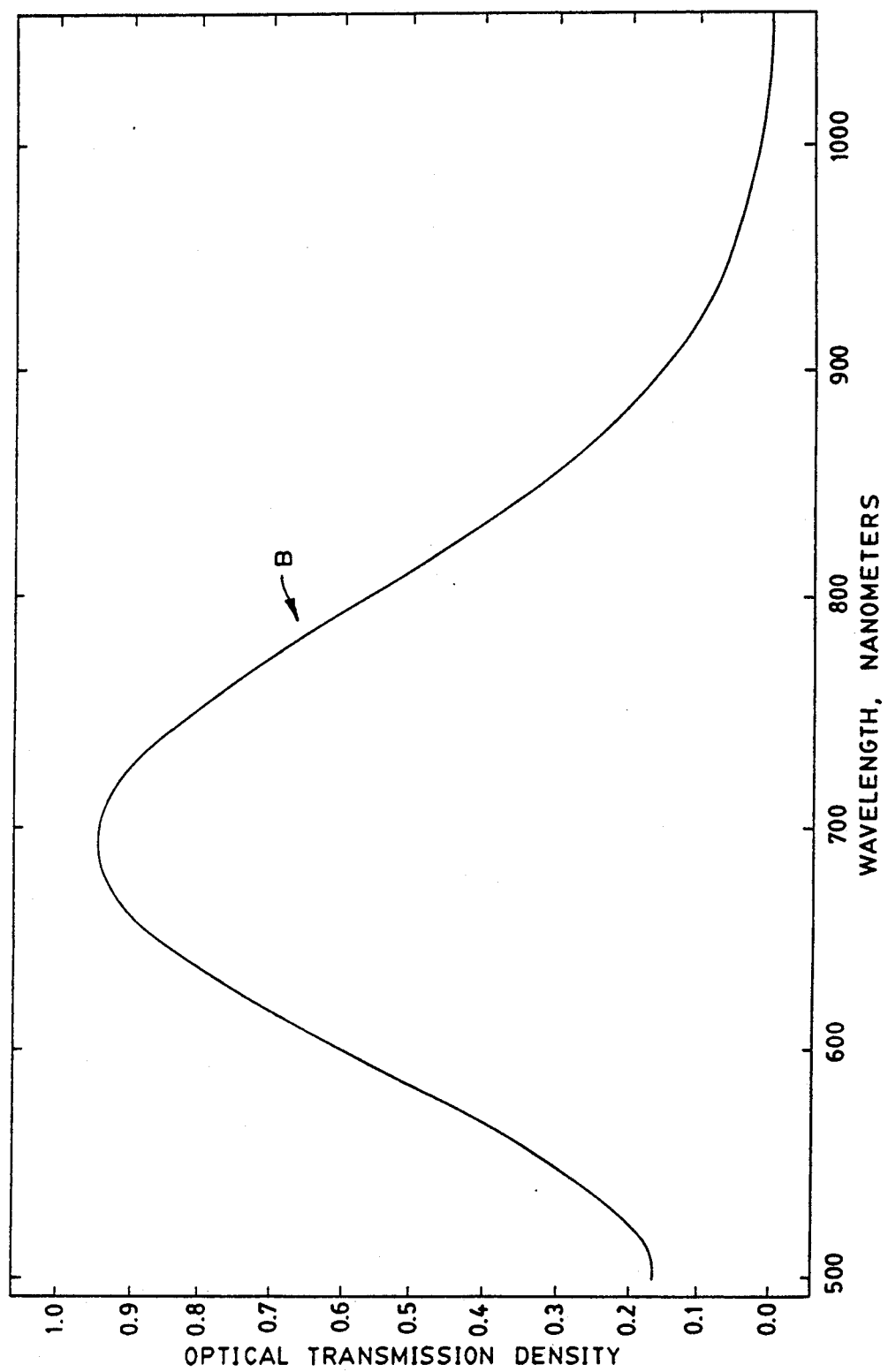
FIGS. 2-7 are graphic illustrations of the spectral absorption characteristics of indicator dyes of the present invention designated as optical filter agents A through G representing the optical transmission density, i.e. the absorbance of the respective agents measured over the wavelength range of 400 nm to 1000 nm in aqueous alkaline solution at a pH substantially above their pKa.
Figure 3:
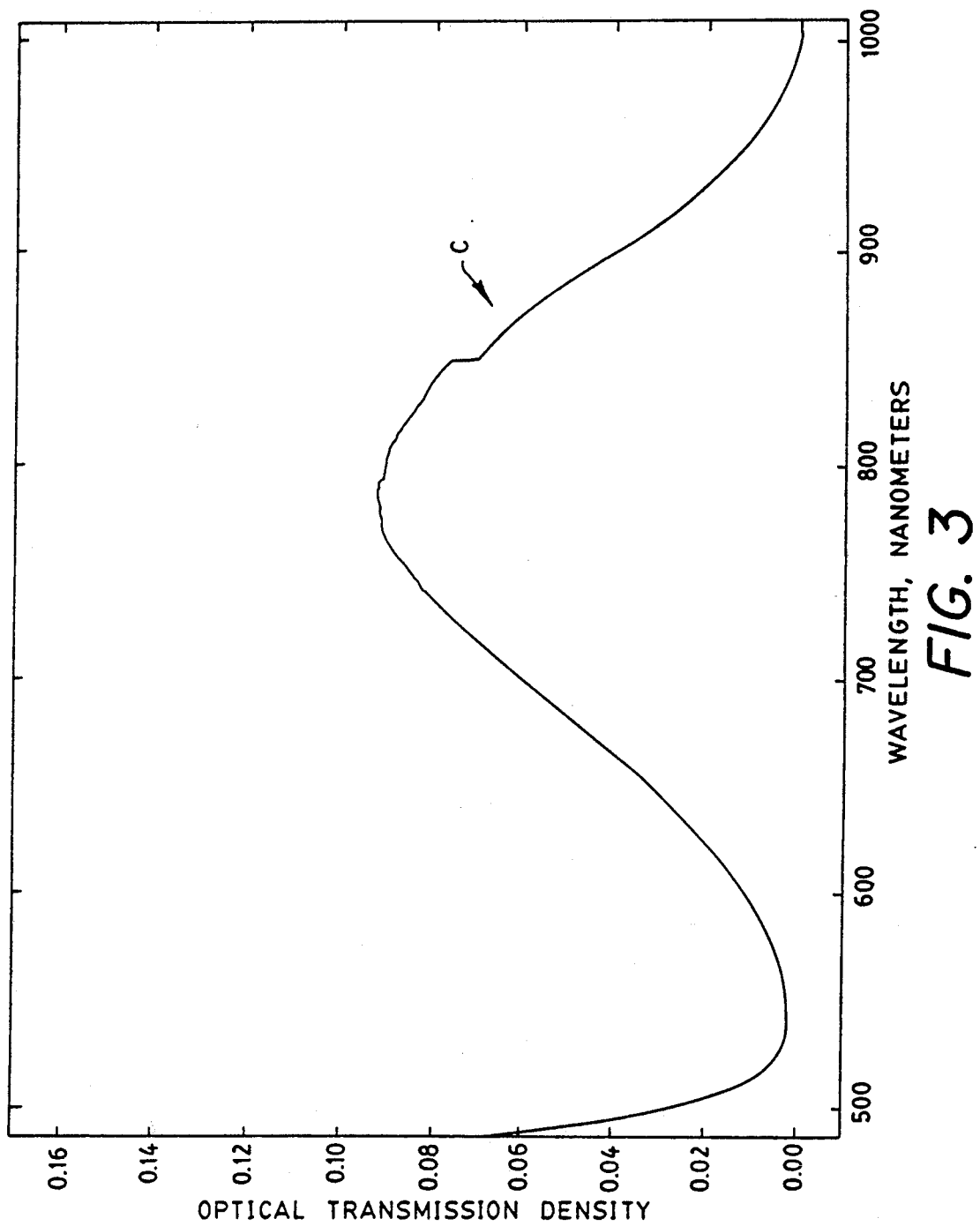
Figure 4:
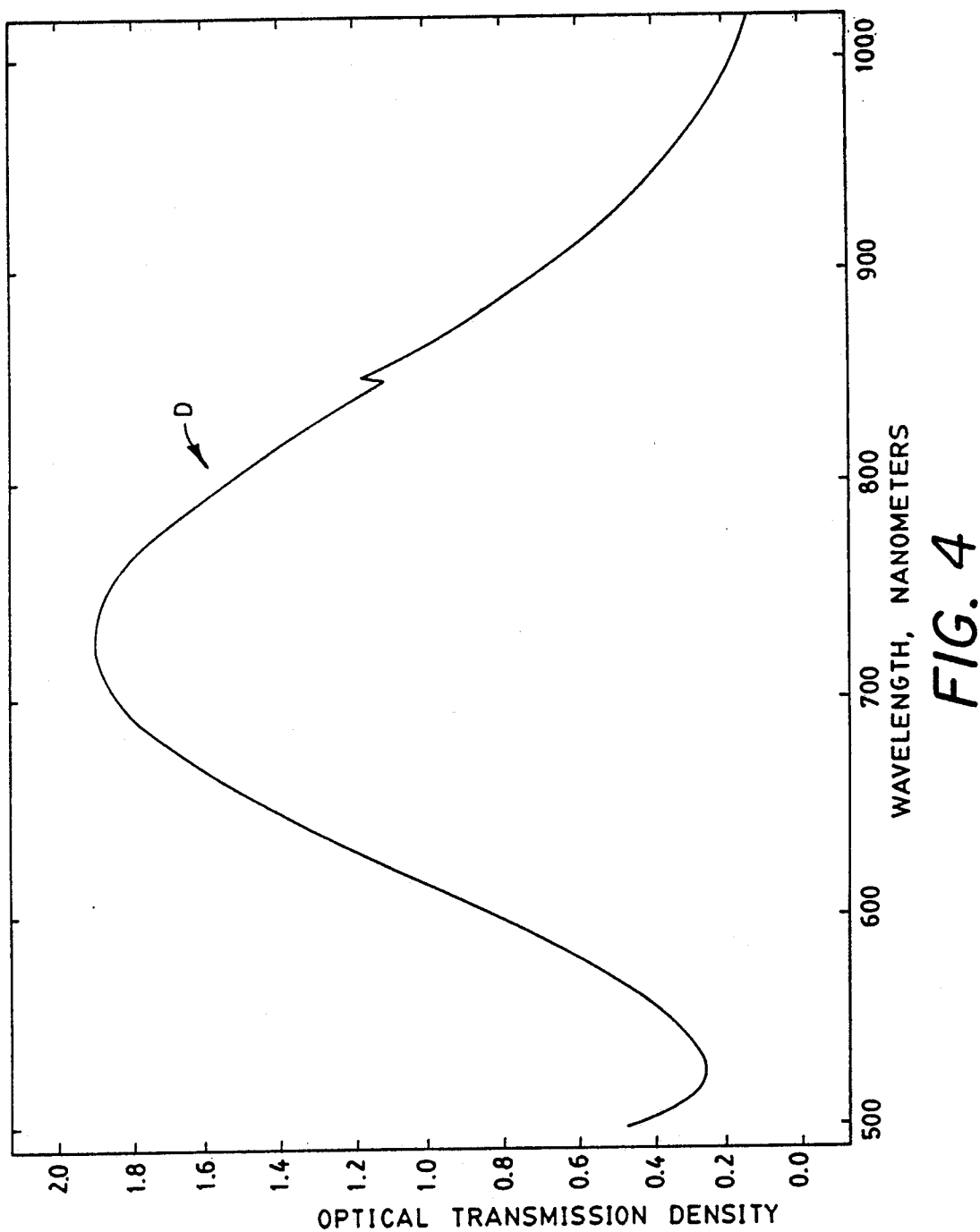
Figure 5:
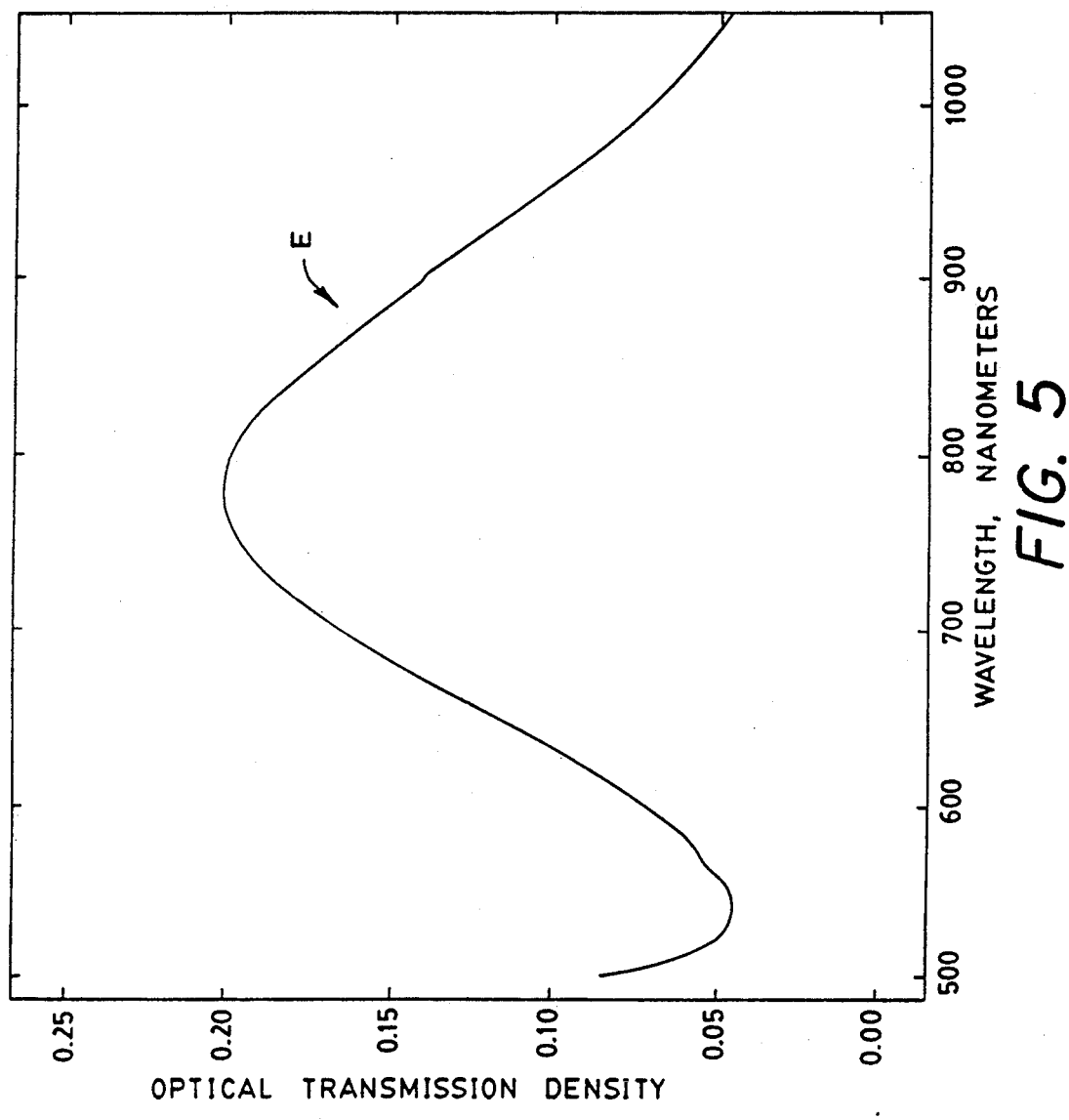
Figure 6:
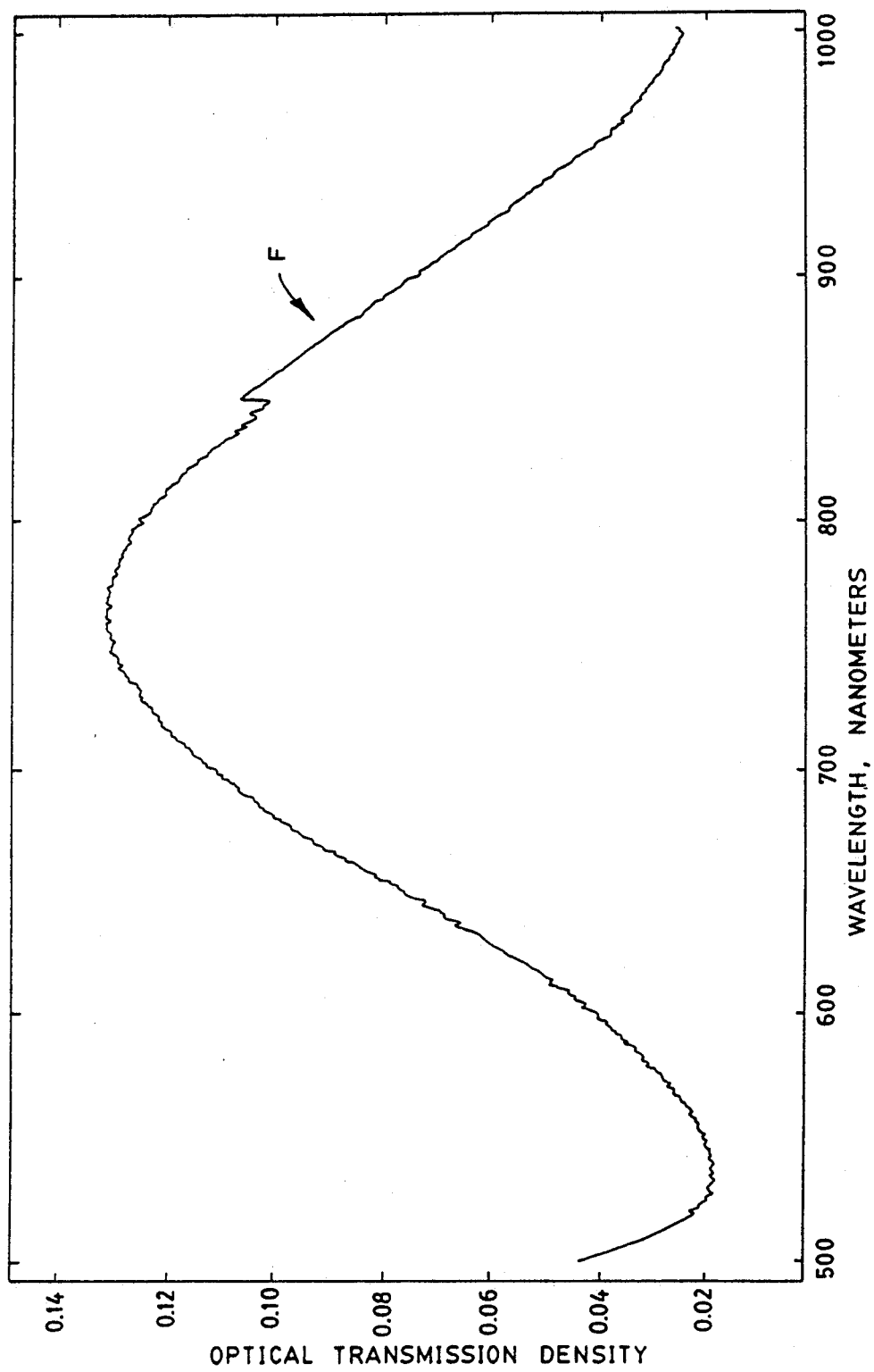
Figure 7:
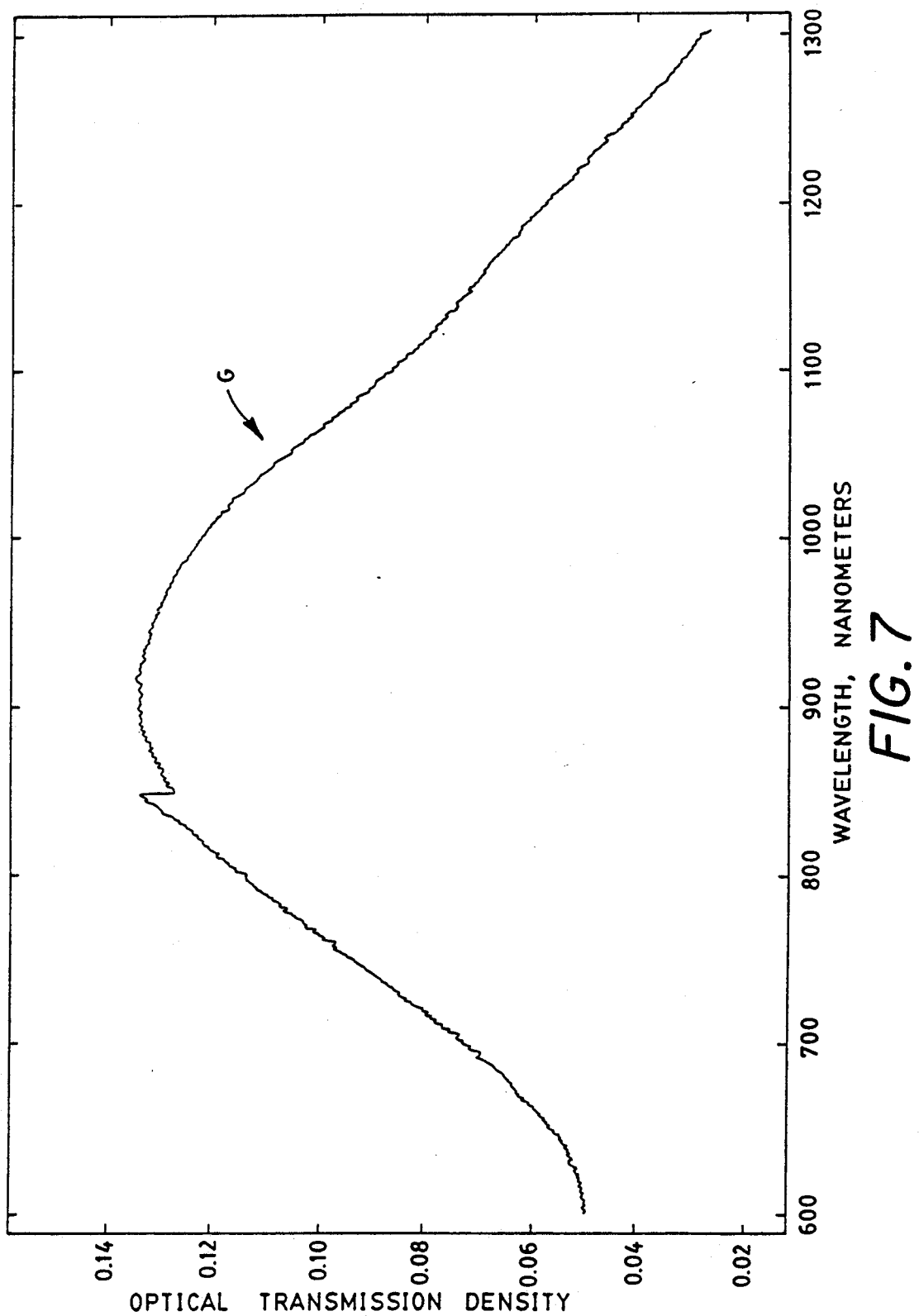

As noted above, novel bridged indicator dyes derived from certain amino-substituted carbocyclic aryl compounds and/or certain hydroxy substituted aryl carbocyclic compounds have been found which have absorption in the near infrared region of the spectrum. These bridged indicator dyes, because they absorb in the near infrared, are useful as optical filter agents in photographic processes for affording protection of a selectively exposed photosensitive material from incident radiation in the near infrared region of the spectrum.

These bridged indicator dyes may be represented by the formula

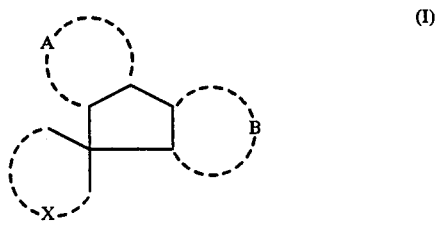

(I)

wherein A and B are selected from a first and second carbocyclic aryl radical, e.g. of the benzene, naphthalene or phenanthrene series, each possessing as a substituent an amino or hydroxy group wherein said substituent is positioned ortho or para to the meso carbon and meta to the bridging carbon, provided further that at least one of said A or B contains as said substituent a hydroxy group, and preferably both contain as said substituent a hydroxy group; and X represents the atoms necessary to complete a ring closing moiety. The amino group may be unsubstituted, mono- or disubstituted and may be substituted with such groups as, e.g., branched or straight chain alkyl having 1 to 8 carbon atoms; aryl, such as phenyl; alkaryl, such as tolyl and ethylphenyl; aralkyl, such as benzyl and phenethyl; or it may be substituted with the atoms necessary to complete a ring system, e.g., an indolinyl group represented by

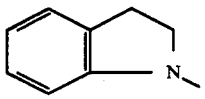

The ring closing moiety may be a phenolate, carboxylate or a sulfinate ester, and is preferably a carboxylate such as a phthalide or naphthalide. The respective phthalide and naphthalide moieties are represented by the formulae:

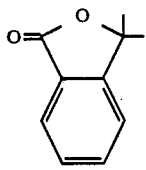

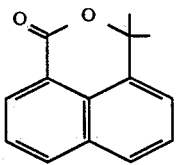

When X represents the atoms necessary to complete a phthalide or sulfinate ester moiety, and the phthalide or sulfinate ester moiety is substituted in the 7'-position so that the compounds of Formula I contain the thermochromic system represented by the formula

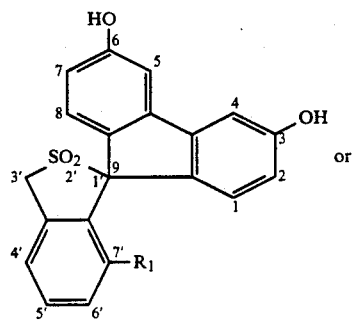

(a)

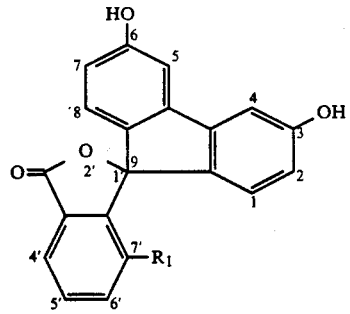

(b)

wherein $R_1$ represents a group which exerts a steric influence such that the lactone or sulfone, at a pH at or above its pKa, remains substantially closed at room temperature but upon the application of heat overcomes said steric influence so that ring opening and hence color formation occurs, the compounds exhibit thermochromism. Representative $R_1$ groups include substituted or unsubstituted alkyl, aryl or alkoxy, or together with a group substituted on the 6'-position of the phthalide or sulfone moiety represents the atoms necessary to complete a substituted or unsubstituted 5- or 6-membered ring. The thermochromic compounds represented by Formula II, while they are pH-sensitive, are generally not useful as optical filter agents except in situations where heat is available to get sufficiently high absorption in the infrared region. These thermochromic compounds form the subject matter of the copending U.S. patent application of M. M. Kampe, D. P. Waller, and D. C. Whritenour, Ser. No. 07/747,643 filed concurrently herewith.

However, when certain substituents other than those defined by $R_1$, e.g. bromine or carboxy, are substituted in the 7'-position of the phthalide or sulfinate ester moiety, the compounds in base, are colored at room temperature which color intensifies upon heating. Presumably these substituents, i.e. bromine and carboxy, exert some steric interference at room temperature so that an equilibrium exists between the closed and opened form of the phthalide or sulfinate ester moiety. These compounds behave as normal pH-dependent indicator dyes at room temperature and also as thermochromic compounds and hence would be useful in applications employing indicator dyes and/or thermochromes. Thus, for example, the compound of example 20, below, spiro[3,6-dihydroxyfluorene-7'-carboxy-9,1'-phthalan]-3'-one in 1 N potassium hydroxide exhibits some color at room temperature, which color intensifies upon heating. The color disappears completely upon cooling in dry ice. The molar absorptivity, $\epsilon$, measured at various temperatures, of a solution of the compound of example 20 in 1 N potassium hydroxide at ~800 nm is reported in Table I below:

TABLE I

| Temp (°C.) | $\epsilon$ |
|---|---|
| −77 | 0 |
| 25 | 550 |
| 66 | 1100 |
| 80 | 1300 |

The compound of Example 12, spiro[2,7-dicarboxy-3,6-dihydroxyfluorene-4',5',6'-7'-tetrabromo-9,1'- phthalan]-3'-one, in 1 N hydroxide had a measured $\epsilon=1230$ at room temperature and $\epsilon=4100$ at 80° C. (both measured at $\lambda max=797$).

It should be noted that when X represents the atoms necessary to complete a phthalide or sulfinate ester moiety, substitution in the 7'-position has been found to impart enhanced base stability to the compounds of Formula I.

The compounds represented in Formula I may contain substituents other than those specified provided they do not interfere with the function of the compounds as opacifying dyes. The A and/or B radicals and/or the ring-closing moiety may be substituted, for example, with solubilizing groups, e.g. carboxy and sulfo groups, to enhance the solubility of the indicator dye in the particular processing composition employed; with a long chain substituent, e.g. a long chain alkoxy group to render the subject dyes less diffusible so that diffusion to the image receiving layer is minimized; with hydrogen bonding groups to adjust the pKa of the indicator dye for the particular processing conditions employed; and with other substituents, such as alkyl groups, which do not interfere with the photographic function of the indicator dye as an optical filter agent. Typical substituents include branched or straight chain alkyl, such as methyl, ethyl, isopropyl, t-butyl, octyl, hexadecyl, and eicosanyl; aryl, such as, phenyl and naphthyl; alkaryl, such as tolyl, ethylphenyl, and p-dodecylphenyl; aralkyl, such as, benzyl, phenethyl, and phenylhexyl; alkoxy, such as, methoxy, ethoxy, butoxy, 1-ethoxy-2-($\beta$-ethoxyethoxy) and octadecyloxy; aryloxy, such as, phenoxy and naphthoxy; alkoxyalkyl, such as methoxyethyl, ethoxyethoxyethyl and dodecyloxyethyl; halo, such as, fluoro, bromo and chloro; sulfo; carboxy; hydroxy; and amino including mono- and di-substituted amino, e.g., N-alkylamino and N,N'-dialkylamino. Such substituents may be substituted on the A and/or B radical and/or on the ring-closing moiety.

In addition to the above, the substituent may comprise a fused ring. For example, the A and/or B radical may contain as a substituent, a cycloaliphatic or an aromatic ring usually having 5 or 6 members, carbocyclic or heterocyclic and substituted or unsubstituted, bonded to adjacent carbon atoms, e.g.,

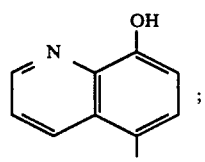

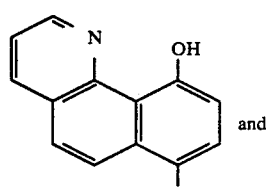 and 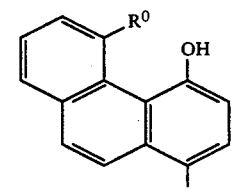

wherein R. is, e.g. —OH.

Specific examples of the bridged indicator dyes within the scope of the present invention include:

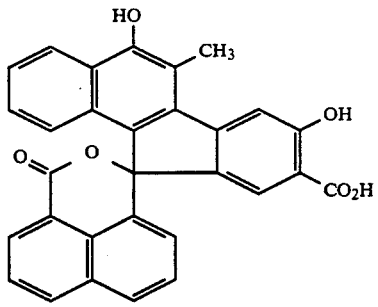 (1)

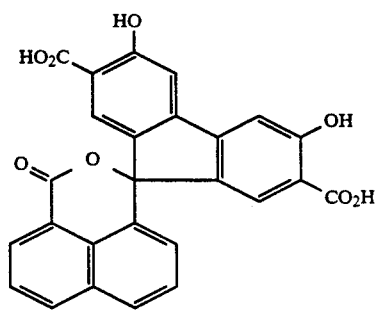 (2)

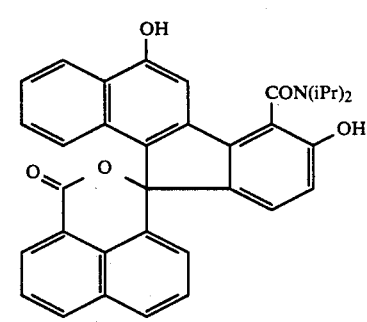 (3)

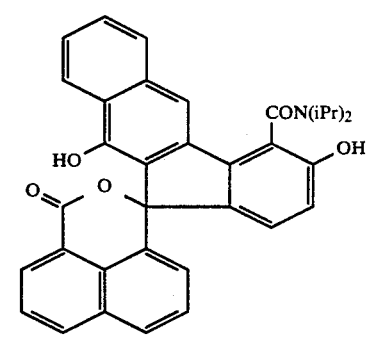 (4)

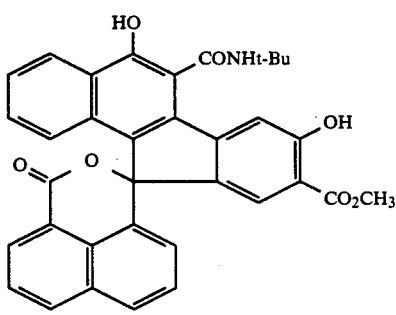 (5)

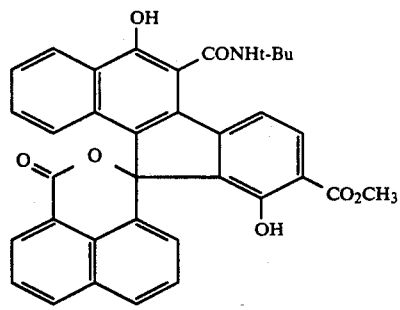
(6)
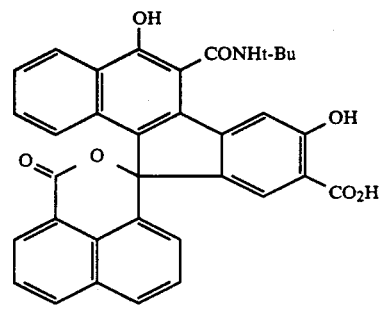
(7)
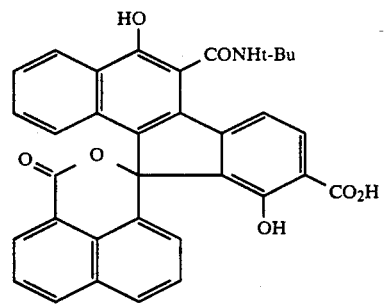
(8)
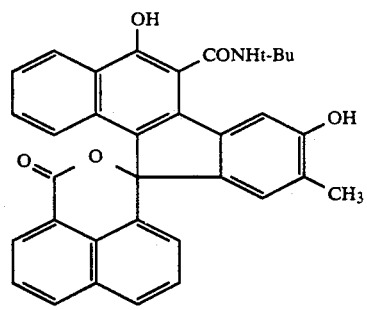
(9)
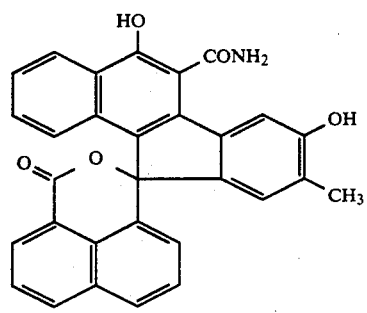
(10)
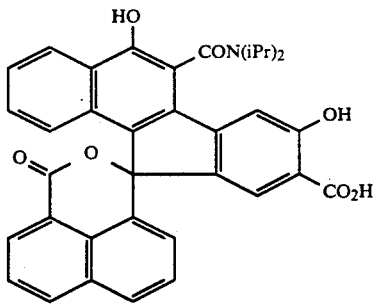
(11)
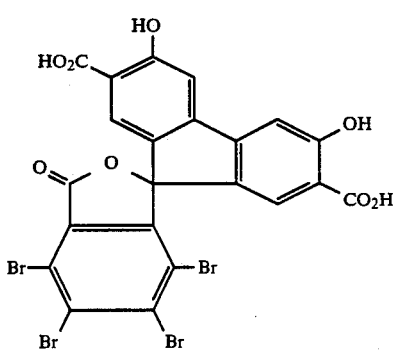
(12)
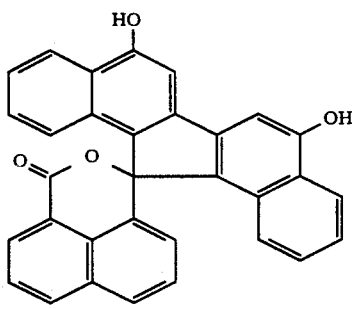
(13)
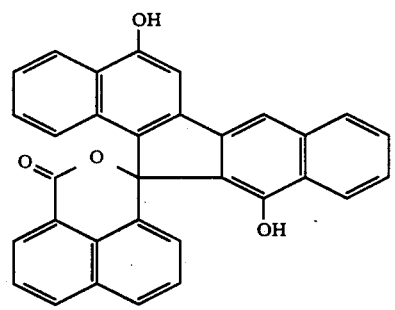
(14)
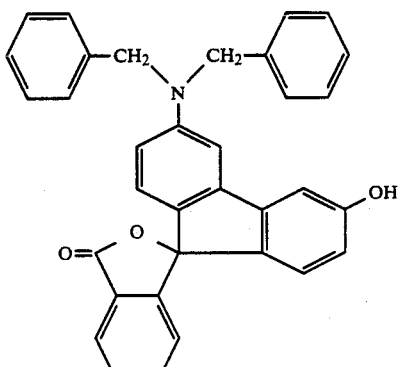
(15)

-continued
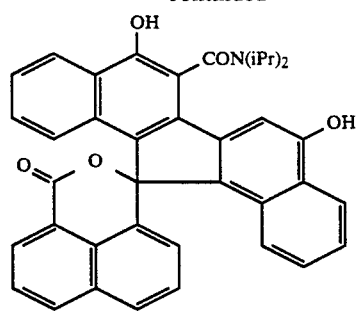 (16)
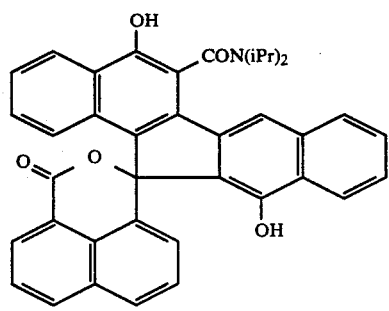 (17)
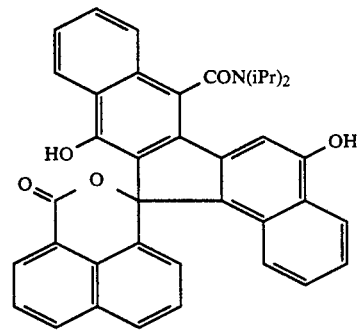 (18)
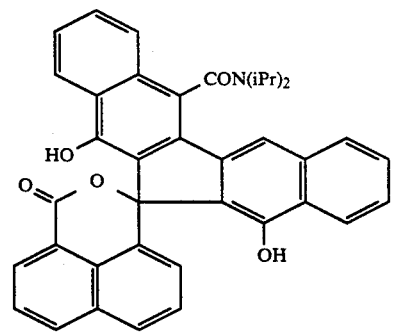 (19)
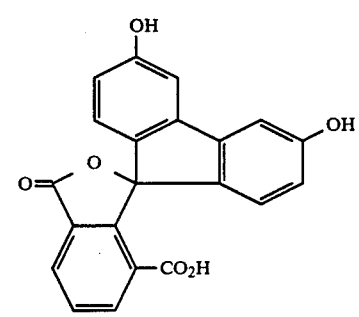 (20)
-continued
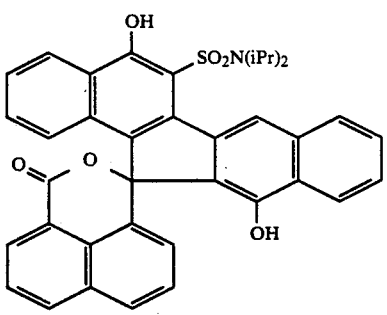 (21)
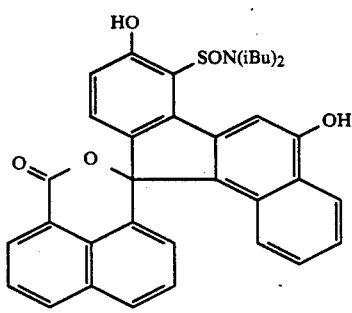 (22)
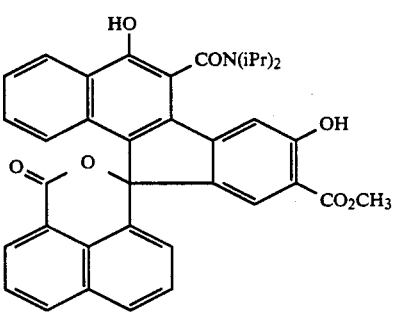 (23)
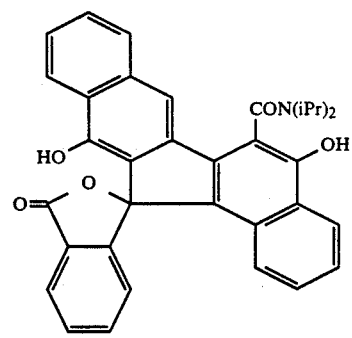 (24)
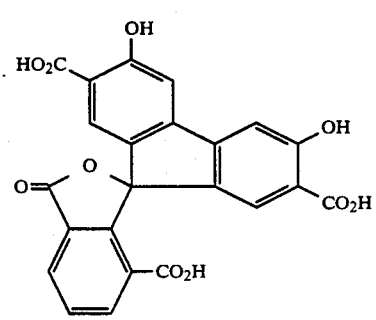 (25)

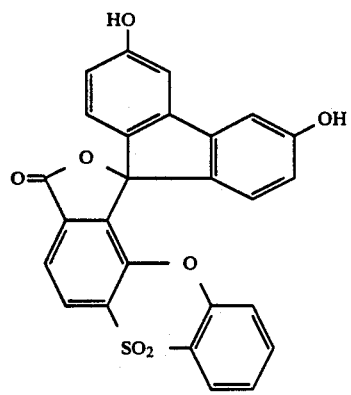

(26)

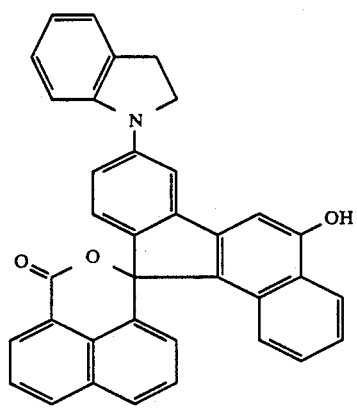

(27)

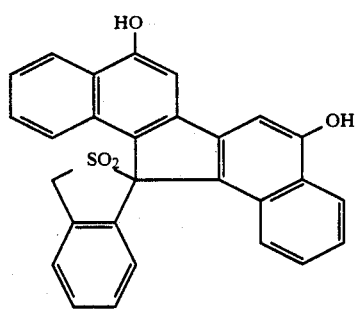

(28)

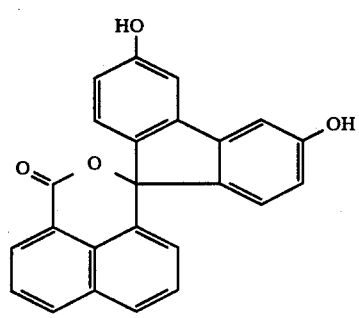

(29)

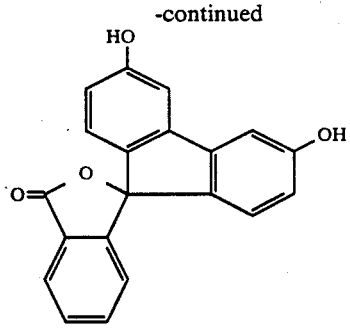

(30)

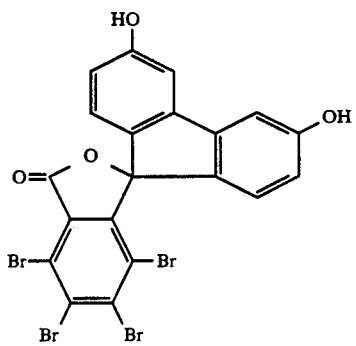

(31)

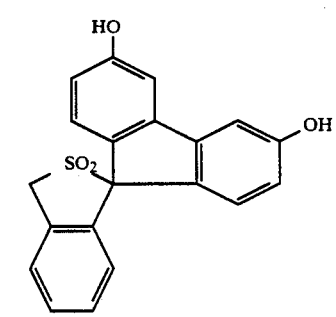

(32)

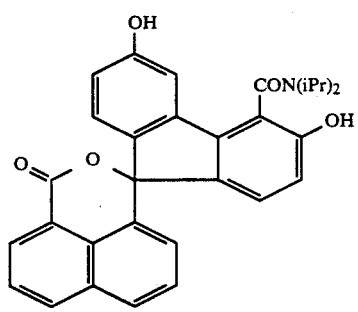

(33)

Various methods may be employed in preparing the indicator dyes described above. The phthalein dyes, i.e., the phthalides and naphthalides, may be prepared by reacting the appropriate 2,2'-dilithio-dimethoxy biaryl with the appropriate phthalic anhydride or 1,8-naphthalic anhydride at reduced temperature, isolating the product and demethylating with boron tribromide to yield the desired bridged phthalein.

Alternatively, the phenols may be protected by conversion to the benzyl ethers instead of the methyl ethers with subsequent deprotection proceeding in trifluoroacetic acid, by conversion to the tertbutyldimethylsilyl (TBDMS) ethers and deprotecting with acetic acid/hydrochloric acid, or by any other suitable means for protecting phenols as suggested, for example, in Greene, T. W., *Protective Groups in Organic Synthesis*, John Wiley & Sons, N.Y., Chs. 2 and 3 (1981) pp. 14-107.

Another method for preparing the bridged phthalides of this invention comprises reacting the appropriate 2,2'-dilithiodimethoxy substituted biaryl or 2,2'-dilithio-5-methoxybiaryl with the appropriate phthalide at a reduced temperature. The isolated product is then oxidized with potassium permanganate and the methyl ethers demethylated by reaction with boron tribromide to yield the desired bridged phthalide. The phenols may also be protected by using any other suitable means as discussed above.

A preferred method of synthesizing the bridged naphthalides of this invention involves a Friedel-Crafts alkylation whereby the appropriately substituted hydroxy biaryl is reacted with 3,3-naphthaloyl dichloride in the presence of aluminum chloride to generate the desired bridged naphthalide.

A further method for preparing the indicator dyes of this invention involves the addition of an ortho-metallated amido substituted arene to an appropriately substituted fluorenone. The substituted fluorenones can be prepared by either an acid catalyzed intramolecular cyclization of the appropriate orthobiarylcarboxylic acid or by an intramolecular nucleophilic addition to a suitably substituted carboxyl derivative under basic conditions.

The synthesis of the necessary biaryls may be realized in a number of ways. One such method, particularly useful for preparing unsymmetrical biaryls, is the palladium catalyzed coupling of the appropriate arylboronic acid with the appropriate arylhalide or aryltriflate in the presence of an auxiliary base. Another method, useful for synthesizing symmetrical biaryls, is the reductive dimerization of aryl halides in the presence of copper bronze. Equally useful for the preparation of both symmetrical and unsymmetrical biaryls is the nickel catalyzed coupling of aryl halides with aryl Grignard reagents. A fourth method, beneficial for synthesizing ortho-biarylcarboxylic acids, involves the coupling of an appropriate aryl Grignard reagent with an appropriate aryl methoxy compound containing an activating oxazoline moiety in a position ortho to said methoxy group. Subsequent hydrolysis under alkaline conditions yields the desired ortho-biaryl carboxylic acid. These and other methods for synthesizing the necessary biaryls are described in G. Bringmann, R. Walter, and R. Weirich, Angew. Chem. Int. Ed. Engl., 29, 977 (1990) and citations therein.

The bridged indicator dyes of Formula I wherein X represents the atoms necessary to complete a sulfinate ester can be prepared by reacting the appropriate benzyl halide with sodium sulfide followed by subsequent oxidation to yield the desired bridged indicator as represented below:

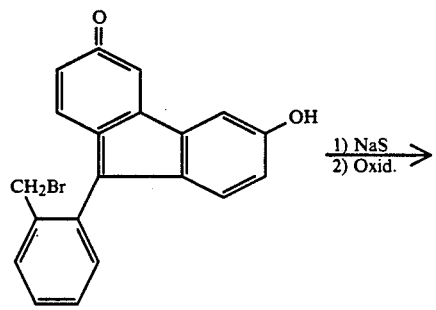

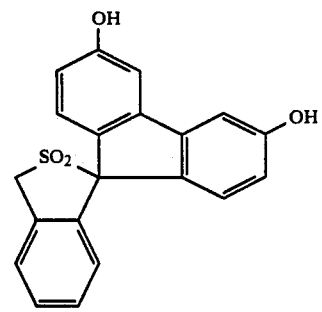

The benzyl halide can be synthesized by reacting a 2,2'-dibromodimethoxybiaryl with n-butyllithium to generate the corresponding 2,2'-dilithio-dimethoxybiaryl. The dilithio compound is reacted with an appropriate phthalide to form a 5-membered cyclic ether. The cyclic ether is treated with boron trihalide to yield the desired benzylhalide.

The following examples are given to illustrate the invention and are not intended to limit the scope thereof. The λmax and epsilon (ε) values reported for each of the compounds below were measured in a 1 N hydroxide solution.

EXAMPLE 1

Preparation of Compound (1) having the formula

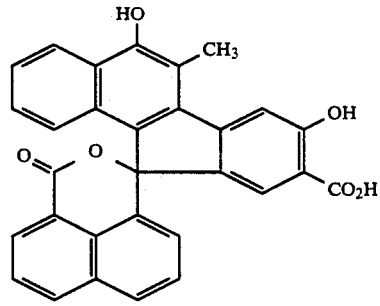

(1) To a solution of 25 grams of niobium (III) chloride-dimethylether complex in 750 mL of tetrahydrofuran was added 10 g of 1-(trimethylsilyl)-1-propyne. The resulting solution was heated gently to reflux overnight and then cooled to 0° C.. A solution of 10 g of phthalic dicarboxaldehyde dissolved in 20 mL of tetrahydrofuran was added to the cooled solution via syringe, and then stirring continued at 0° C. for 3 hours. The resulting solution was extracted with 3×75 mL of 10% sodium hydroxide until most of the dark color had dissipated and the aqueous washes were then back extracted with 3×75 mL of methylene chloride. The organic layers were combined, dried over magnesium sulfate, filtered and concentrated. The resulting dark oil was flash filtered through acetone washed silica using methylene chloride. Those fractions containing product were combined and concentrated under vacuum to give 11.3 g of 2-methyl-3-tetramethylsilyl-1-naphthol as a yellow oil.

(2) 11.3 g of 2-methyl-3-tetramethylsilyl-1-naphthol was dissolved in 18 mL of pyridine and cooled to 0° C.. To this cooled solution was added dropwise 6 mL of acetic anhydride, and the resulting mixture was allowed to stir at room temperature overnight. The reaction mixture was diluted with 250 mL of methylene chloride and washed with 8×75 mL of a saturated copper sulfate solution. The aqueous fractions were combined and back extracted with 3×50 mL of methylene chloride. All of the organic layers were combined, washed with 50 mL saturated sodium chloride, dried over magnesium sulfate, filtered, and concentrated. The resulting dark oil was flash filtered through acetone washed silica using methylene chloride to give 11 g of O-acetylated 2-methyl-3-tetramethylsilyl-1-naphthol as a pale yellow oil.

(3) To 11.5 g of O-acetylated 2-methyl-3-tetramethylsilyl-1-naphthol dissolved in 300 mL of methylene chloride and cooled to −78° C. was added dropwise 12 mL of boron tribromide. The resulting mixture was warmed to 25° C. overnight. The solution was recooled to −78° C. and quenched with 100 mL of methanol. The solvents were removed under vacuum and 100 mL of 10% hydrochloric acid was added to the residue. This was then extracted with 8×60 mL of methylene chloride. The organic layers were combined, dried over magnesium sulfate, filtered and concentrated to yield 5.8 g of the aryl boronic acid as a dark oil.

(4) To a degassed solution of 9.4 g of methyl 4-iodo-2-methoxybenzoate in 300 mL of toluene and 120 mL of 2 M sodium carbonate was added 1.8 g of tetrakis(triphenylphosphine) palladium(0). After stirring for 15 minutes, 5.8 g of the aryl boronic acid, prepared in step 3, in 120 mL of methanol was added. The resulting mixture was heated at 45° C. for 48 hrs. The organic layer was separated and the aqueous layer was extracted with toluene. The organic layers were combined, dried over magnesium sulfate, filtered and concentrated. The residual dark oil was purified by flash chromatography (2:1 methylene chloride:hexane as eluent). The fractions containing product were combined and concentrated to give a yellow solid. The yellow solid was recrystallized from hexane to give 7.2 g of 2-methyl-3-(4'-methoxycarbonyl-3'-methoxyphenyl)-1-naphthol as a white solid.

(5) To a cooled (-78° C.) suspension of 7.0 g of 2-methyl-3-(4'-methoxycarbonyl-3'-methoxyphenyl)-1-naphthol in 100 mL of methylene chloride was added, dropwise over 10 minutes, 26 mL of 1 M boron trichloride in methylene chloride. The resulting mixture was stirred overnight at 25° C. and then quenched with 25 mL of methanol. The solution was washed with 3×40 mL of 1 N hydrochloric acid and then 2×50 mL of saturated sodium bicarbonate. The organic layer was dried over magnesium sulfate, filtered and concentrated. The residual oil was purified by flash chromatography (2:1 methylene chloride:hexane as eluent) to give 4.8 g of 2-methyl-3-(4'-methoxycarbonyl-3'-hydroxyphenyl)-1-naphthol as a white solid.

(6) To a suspension of 6 g of 1,8-naphthalic anhydride in 75 mL of o-dichlorobenzene was added 7.5 g of phosphorous pentachloride. The resulting solution was heated at 140°-155° C. overnight. After cooling to 0° C., 9 g of aluminum chloride was added, and stirring was maintained at 0° C. for 30 minutes. To the cooled (0°) solution was added 6.2 g of 2-methyl-3-(4'-methoxycarbonyl-3'-hydroxyphenyl)-1-naphthol in 75 mL of o-dichlorobenzene. The resulting mixture stirred at 0° C. overnight and was quenched by pouring into 200 mL of a 3 N sodium hydroxide solution. The organic layer was separated and extracted with 3×30 mL 3 N sodium hydroxide. The combined aqueous layers were extracted with 3×75 mL of methylene chloride. The aqueous layer was poured into 400 mL of ice-cold 6 N hydrochloric acid. The precipitated solids were collected by suction filtration. The solids were recrystallized by dissolving in tetrahydrofuran and adding 2 volumes of acetonitrile followed by distillation of tetrahydrofuran until the solution became cloudy. The mixture was stirred, uncovered, for 5 days and then filtered. Recrystallization from ethylacetate gave 1.7 g of Title Compound (1), λmax=652 nm (ε=4324). The structure was confirmed by NMR and mass spectroscopy.

The methyl 4-iodo-2-methoxybenzoate employed in Example 1 above was synthesized as set out below:

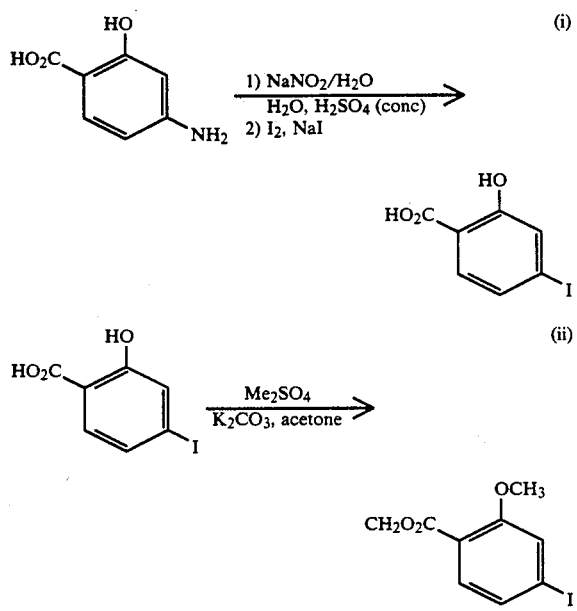

(i) A solution of 20 g of 4-aminosalicylic acid in 250 mL of water and 120 mL of concentrated sulfuric acid was cooled to 0°. To this chilled solution was added, dropwise over a 30-minute period, 10 g of sodium nitrite dissolved in 15 mL of water. The resulting solution was stirred at 0° C. for 90 minutes and then transferred via canulla to a solution of 40 g of iodine and 45 g of sodium iodide in 60 mL of water maintained at 0° C. This was stirred at 0° C. for an additional 6 hours and then allowed to warm to room temperature overnight. Sodium sulfite was added until the solution turned yellow. The precipitate was filtered and recrystallized from 200 mL of acetonitrile to yield a first crop of 13 g and a second crop of 6.2 g of 2-hydroxy-4-iodobenzoic acid as a light tan solid.

(ii) 170 g of potassium carbonate was added to a 0° C. solution of 148 g of 2-hydroxy-4-iodobenzoic acid dissolved in 650 mL of acetone. Gradually, over a period of 20 minutes while maintaining the temperature at 0° C., 108 mL of dimethylsulfate was introduced. The resulting suspension was stirred at room temperature for 1 hour and was then refluxed for 4 hours. The mixture was cooled to 25° C. and filtered. The solvent was concentrated to yield a dark oil which was purified by distillation to yield 106 g of methyl 4-iodo-2-methoxy benzoate as a colorless oil (bp 105°-112° C. C @0.2 Torr).

EXAMPLE 2

Preparation of Compound (2) having the formula

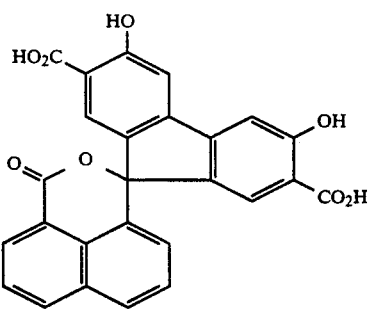

To a mechanically stirred suspension of 90 g of copper powder in 450 mL of dimethylformamide was added 90 g of methyl 4-iodo-2-methoxybenzoate (which was prepared as in Example 1). The resulting mixture was heated at reflux for 6 days and then cooled to room temperature and diluted into 1500 mL of chloroform. The mixture was filtered and the copper was washed with 2×150 mL of chloroform. The residual copper was suspended in 2 liters of water and extracted with 6×150 mL of chloroform. All the organic fractions were combined, dried and concentrated to approximately 250 mL. The concentrate was cooled to 0° C. and the precipitate filtered to give 33 g of 3,3'-dimethoxy-4,4'-bis(methoxycarbonyl)biphenyl as a pale yellow powder. Deprotection of the dimethoxy compound was accomplished with boron trichloride according to step 5 of Example 1 to yield 3,3'-dihydroxy-4,4'-bis(methoxycarbonyl)biphenyl. The structure was confirmed by NMR.

To a slurry of 14 g of naphthalic anhydride and 75 mL of o-dichlorobenzene was added 23 g of phosphorous pentachloride. The mixture was mechanically stirred at 145°-155° C. Cfor 6 hours, cooled to 10° C., and then 20 g of aluminum chloride was added with rapid stirring. Stirring was continued at 10° C. for 30 minutes, at which time a suspension of 18 g of 3,3'-dihydroxy-4,4'-bis(methoxycarbonyl)biphenyl in 50 mL of o-dichlorobenzene and 50 mL of nitrobenzene was added. The reaction mixture was warmed to room temperature over a period of one hour and then heated at 60°-80° C. for 3 days. The reaction was quenched by pouring onto 500 g of ice diluted with 750 mL of methylene chloride and complete hydrolysis effected by heating at reflux. The aqueous layer was extracted with 3×75 mL of methylene chloride. The organic layers were combined, washed with water and concentrated in vacuo to approximately 250 mL. The residual oil was filtered through silica, first with methylene chloride and then with 10:1 methylene chloride:acetone as eluents. The appropriate fractions were combined and concentrated to give a yellow solid which was recrystallized from 275 mL of acetonitrile to yield 14.24 g of the dimethylester of Title Compound (2), as a pale yellow solid.

14 g of the dimethylester was dissolved in 300 mL of isopropanol with heating on a steam bath. While rapidly stirring, a solution of 56 mL of 50% NaOH in 300 mL of water was added all at once. The solution, which immediately turned dark green, was heated at 45°-60° C. for 6 hours and then cooled to 25° C. The layers were separated and the aqueous layer was precipitated by pouring into 250 mL of 1 N hydrochloric acid. The precipitate was collected by filtration and recrystallized from tetrahydrofuran and acetonitrile. The recrystallization was repeated several times to yield 5.8 g (45%) of the Title Compound (2) as a white solid, λmax=791 nm (ε=1200). The structure was confirmed by NMR and mass spectroscopy.

EXAMPLES 3 AND 4

Preparation of Compounds (3) and (4) having the formula

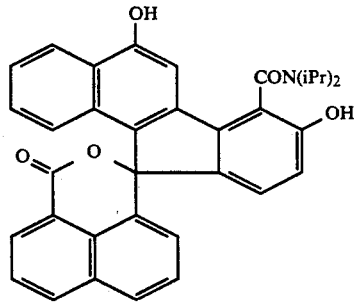

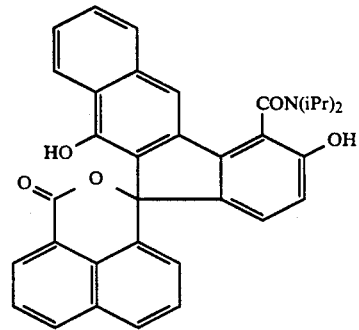

100 g of o-anisic acid was dissolved in 80 mL of thionyl chloride followed by the addition of 2 drops of dimethyl formamide. After stirring at 25° C. overnight, the excess thionyl chloride was removed under vacuum (aspirator). The resulting residue was diluted with methylene chloride and cooled to 0° C. To the cooled solution was added, dropwise, 185 mL of diisopropylamine over a 2-hour period. After the addition was complete, the reaction mixture was warmed to 25° C. and diluted to 1 1 with methylene chloride. The precipitated amine salts were filtered, and the solution was washed with 2×150 mL of 1 N hydrochloric acid, 1×150 mL of saturated sodium bicarbonate, and 1×50 mL of saturated sodium chloride. The organic solution was dried over anhydrous magnesium sulfate, filtered and concentrated to a slurry (~100 mL). The white precipitate was filtered and dried to yield 87 g of o-methoxy-N,N-diisopropylbenzamide. The structure was confirmed by NMR.

20 g of o-methoxy-N,N-diisopropylbenzamide was dissolved in 450 mL of tetrahydrofuran and the resulting solution was cooled to −78° C. To the solution at −78° C. was added 50 mL of a 1.7 M solution of t-butyllithium/hexanes over a 5 minute period. The reaction mixture was stirred at −78° C. for an additional 2 hours resulting in a thick white slurry. The anion was quenched by the addition of 12 mL of trimethyl borate. The solution was warmed to 25° C. and the tetrahydrofuran was removed in vacuo. The resulting mixture was diluted with 150 mL of methylene chloride and then washed with 3 ×25 mL of 10% hydrochloric acid. The aqueous washings were back extracted with 2×25 mL of methylene chloride. The combined methylene chloride extracts were dried over anhydrous magnesium sulfate, filtered and the solvent was removed to yield 2-N,N-diisopropylcarbamoyl-3-methoxyphenyl-1-boronic acid.

The 2-N,N-diisopropylcarbamoyl-3-methoxyphenyl-1-boronic acid was coupled with 3-iodo-1-methoxynaphthalene in the presence of tetrakis(triphenylphosphine) palladium (0) in a manner analogous to that described in step 4 of Example 1, above. Recrystallization from methylene chloride yielded 16.2 g of 3-(3'-methoxy-2'-N,N-diisopropylcarbamoylphenyl)-1-methoxynaphthalene as an off-white solid. The structure was confirmed by NMR. The dimethoxy biaryl was demethylated in a stepwise fashion by reaction with boron trichloride as in step 5 of Example 1 followed by reaction with boron tribromide. 3 g of the resulting dihydroxy biaryl was reacted with 3,3-naphthaloyl dichloride in the presence of aluminum chloride in a manner analogous to that done in Example 1. Purification was accomplished by flash chromatography (18:1 methylene chloride:acetone as eluent) to yield 320 mg of the Title Compound (3), $\lambda$max = 728 nm (e=930) and 28 mg of the Title Compound (4), $\lambda$max=664 nm ($\epsilon$=10,100). The structures were confirmed by NMR and mass spectroscopy.

The 3-iodo-1-methoxynaphthalene used in synthesizing compound (3) above was prepared as set out below:

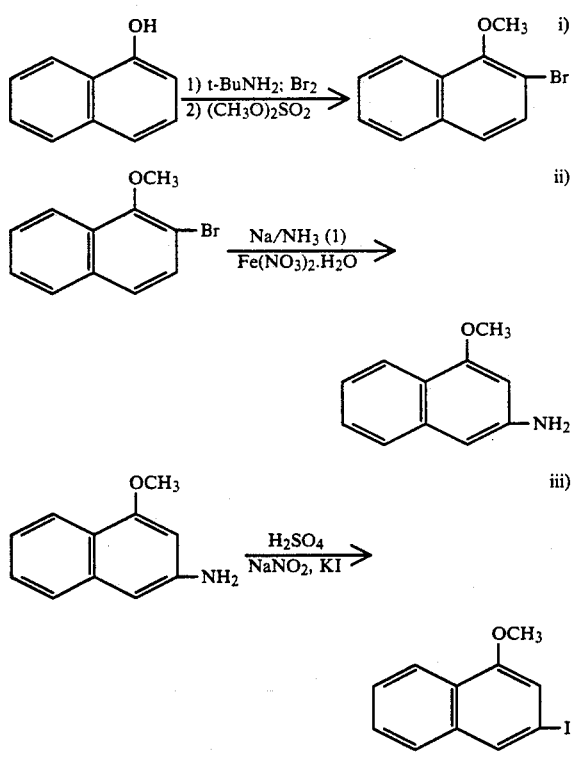

i) 1-naphthol was converted into 2-bromo-1-naphthol by reaction with a slurry of N-bromo-t-butylamine at $-78°$ C. according to the procedure described in Pearson, Wysong, Breder, J. Org. Chem. 32, 2358 (1967). To a solution of 1 mole (crude) of the bromonaphthol in 750 mL of acetone was added 175 g of potassium carbonate. Over a 2-hous period, 95 mL of dimethylsulate was added dropwise to the mechanically stirred reaction mixture. The resulting slurry was stirred at 25° C. overnight. The solids were filtered and the solution was stripped to yield a dark brown oil. Initial purification was accomplished by vacuum distillation (80°–120° C., 0.2 Torr) followed by further purification by HPLC with hexane to yield 145 g of 2-bromo-1-methoxynaphthalene as a pale yellow oil. NMR confirmed the structure.

ii) 20 g of sodium was added to a solution of 1 l ammonia and 500 mg iron (II) nitrate monohydrate at $-50°$ C. The resulting mixture was stirred at $-50°$ C. until the blue color had dissipated and a grey-black suspension appeared ($\sim$1 hr.). 140 g of 2-bromo-1-methoxynaphthalene in 250 mL of ether was added dropwise, over 30 minutes, to the grey-black suspension. After stirring for 6 hours, 120 g of ammonium chloride and 1.5 l of ether were added and the ammonia was allowed to evaporate overnight. The resulting solids were filtered and the filtrate was extracted with 8×75 mL of 2 N hydrochloric acid. The acid washes were neutralized with 3 N sodium hydroxide. The resulting solution was extracted with 12×50 mL of ether. The ether extracts were combined, washed with a brine solution, dried over anhydrous magnesium sulfate, filtered and the ether was removed to yield a dark brown oil. Further purification was accomplished by bulb-to-bulb distillation resulting in 52 g of 3-amino-1-methoxynaphthalene as an orange oil. The structure was confirmed by NMR.

iii) 50 g of 3-amino-1-methoxynaphthalene was added to 750 mL of 6 N sulfuric acid. The mixture was heated to dissolve the naphthalene and the resulting solution was cooled to 0° C. To the resulting slurry of amine hydrosulfate salt at 0° C. was added a solution of 20 g of sodium nitrite in 30 mL of water. The resulting mixture stirred at 0° C. for 1 hour and was then poured into a solution of 100 g of potassium iodide and 20 g of iodine in 400 mL water. After stirring for 1 hour at room temperature, 250 mL methylene chloride was added. The layers were separated and the aqueous portion was extracted with 3×100 mL methylene chloride. The organic portion was combined with the methylene chloride extracts and was washed with 3×75 mL saturated sodium bisulfite, dried over anhydrous magnesium sulfate, filtered, and stripped. The resulting product was pre-adsorbed onto silica and eluted with hexane. The appropriate fractions were combined, concentrated and the residual oil was further purified by HPLC to yield 15 g of 3-iodo-1-methoxynaphthalene as a yellow oil. The structure was confirmed by NMR.

EXAMPLES 5 AND 6

Preparation of Compounds (E) and (F) having the following formulae

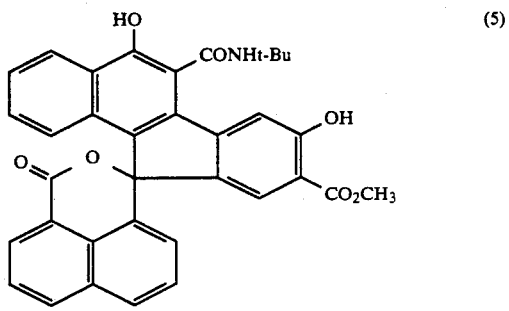

-continued

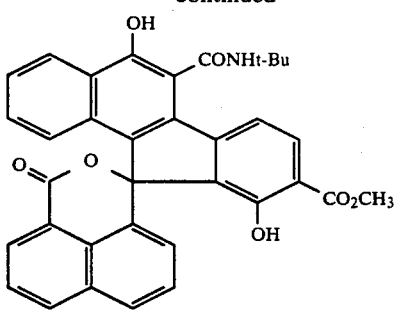
(6)

15.6 g of 1-hydroxy-3-(3'-hydroxy-4'-methoxycarbonylphenyl)-2-N-tert-butylnaphthamide was reacted with 3,3-naphthaloyl dichloride as in Example 1, above, to yield 14.2 g of a 1 6:1 mixture of Title Compounds (5) and (6) after recrystallization from acetonitrile. Subsequent recrystallizations from dimethylsulfoxide resulted in 7.8 g of Title Compound (5), $\lambda$max=730 nm ($\epsilon$=1528). NMR indicated only trace amounts of Title Compound (6) as an impurity.

The dimethylsulfoxide mother liquors from the recrystallizations of compound (5) were combined and poured into water. The resulting precipitate was filtered and dried. Repeated recrystallizations from acetonitrile resulted in 2.6 g of Title Compound (6), $\lambda$max=731 ($\epsilon$=396). NMR confirmed the structure and indicated only trace quantities of Title Compound (5).

The biaryl, 1-hydroxy-3-(3'-hydroxy-4'-methoxycarbonylphenyl)-2-N-tert-butylnaphthamide, used to prepare compounds (5) and (6) was made according to the coupling procedure set out in Example 1, above. The methyl-4-iodo-2-methoxybenzoate was prepared according to the procedure in Example 1. The arylboronic acid was made in a manner analogous to that used to prepare the arylboronic acid of Example 3 except t-butylamine was used in place of the diisopropylamine and 1-methoxy-2-naphthoic acid was used in place of the o-anisic acid.

EXAMPLES 7 AND 8

Title Compounds (5) and (6) above were hydrolyzed in base (1 N KOH) to generate compounds (7) and (8) having the following formulae

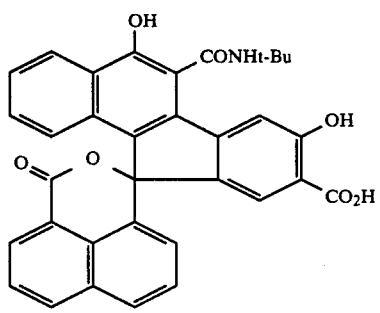
(7)

$\lambda$max = 765 nm ($\epsilon$ = 1670)

-continued

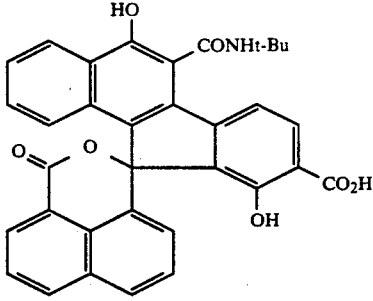
(8)

$\lambda$max = 745 nm ($\epsilon$ = 450)

EXAMPLE 9

Preparation of Compound (9) having the formula

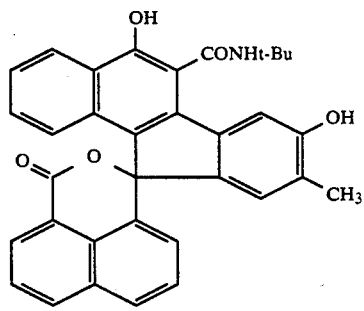

Compound (7) (260 mg) was dissolved in 10 mL of tetrahydrofuran and the solution was cooled to 0° C. Triethylamine (300 $\mu$L) and ethyl chloroformate (180 $\mu$L) were added and the resulting mixture stirred at 0° C. for 1 hour. The solvents were removed in vacuo and a solution of 150 mg of sodium borohydride in 1 mL of methanol was added to the residue. After stirring for 2 hours, the reaction mixture was diluted with 100 mL of water and the resulting mixture was extracted with 3×20 mL methylene chloride. The combined methylene chloride extracts were dried over anhydrous magnesium sulfate, filtered and concentrated. The residue was recrystallized from methylene chloride:acetone (1:1) to yield 112 mg of the corresponding carbonate as a white solid.

To a solution of 25 mL of 3 N sodium hydroxide in 20 mL of isopropanol was added 100 mg of the above carbonate. After stirring at 0° C. for 1 hour, the mixture was warmed to 25° C. and then poured into acidified (hydrochloric acid) ice water. The resulting precipitate was collected by filtration and purified by recrystallization from methylene chloride/hexanes to yield 40 mg of Title Compound (9) as a pale yellow solid, $\lambda$max=780 nm ($\epsilon$=1500). The structure was confirmed by NMR.

EXAMPLE 10

Preparation of Compound (10) having the formula

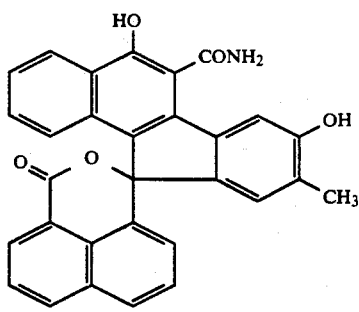

Title Compound (9) was dissolved in 20 mL of methanesulfonic acid and heated at 40°–60° C. for 6 hours. The reaction mixture was quenched by pouring it into water. The precipitated solids were collected by filtration and recrystallized from methylene chloride to yield the Title Compound (10) as a pale yellow solid, $\lambda max=780$ nm ($\epsilon=430$). The structure was confirmed by NMR.

EXAMPLE 11

Compound (11) having the formula

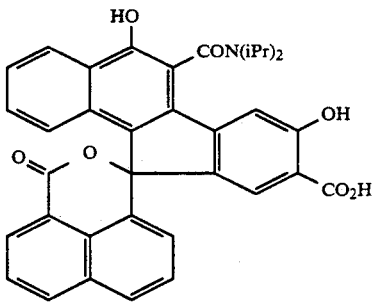

was prepared according to the procedure used to prepare Example 7, except that the biaryl was substituted with a diisopropylamide group in place of the t-butyl amide group. The crude product was purified by flash chromatography using methylene chloride:acetone (40:1) as eluent. Recrystallization from acetonitrile resulted in Title Compound (11), $\lambda=760$ nm ($\delta=1200$). NMR confirmed the structure.

EXAMPLE 12

Preparation of Compound (12) having the formula

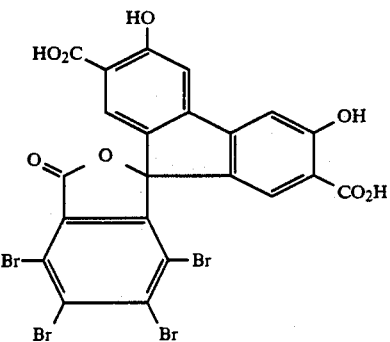

To a slurry of tetrabromophthalic anhydride in 10 mL tetrachloroethane was added 2.2 g phosphorous pentachloride. The resulting mixture was refluxed for ~12 hours and then the heat was increased to distill off the tetrachloroethane and the phosphorous oxychloride which had formed. Upon cooling to room temperature a solid cake was formed to which was added 1.5 g of aluminum chloride and 10 mL of nitrobenzene. The resulting mixture was heated under nitrogen at 70°–75° overnight.

The reaction mixture was diluted with 15 mL nitrobenzene followed by the addition of 4.0 g of aluminum chloride and 2.25 g of 3,3'-dihydroxy-4,4'-bis(methoxycarbonyl)biphenyl (prepared as in Example 2, above). The resulting mixture was heated at 55°–60° C. for 72 hours. After cooling to room temperature, the mixture was diluted to 200 mL with methylene chloride. The resulting off-white precipitate was filtered, washed with hexane and added to a mixture of 25 mL concentrated hydrochloride acid and crushed ice. The resulting white solid was collected by filtration, dried and separated from the starting biphenyl by column chromatography, eluting with methylene chloride, then hexanes:methylene chloride (1:1) and then again with methylene chloride, to yield 0.460 g of pure dimethylester. Further purification of the mixed product yield another 0.490 g of pure dimethyl ester. NMR confirmed the structure.

The dimethyl ester of Title Compound (12) (0.225 g) was suspended in 50 mL of 1 N sodium hydroxide under an atmosphere of nitrogen. The mixture was stirred vigorously for 5¼ hours at room temperature and then cooled to 0° C. The chilled solution was acidified with concentrated hydrochloric acid to yield a white precipitate. The precipitate was extracted into a mixture of ethyl acetate:ether (1:1) and the resulting solution was dried over anhydrous sodium sulfate. The solution was filtered, the solvent removed and the resulting solid dried in vacuo to yield 0.130 g of Title Compound (12) as a white solid, $\lambda=797$ nm ($\epsilon=1230$). The structure was confirmed by NMR and mass spectroscopy.

EXAMPLE 13

Preparation of Compound (13) having the formula

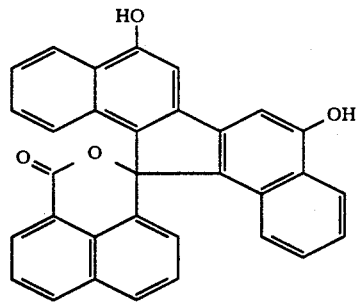

Under an atmosphere of nitrogen, a mixture of 5.0 g of 4-methoxy-1-naphthol and 50 mL chloroform was mechanically stirred with 10.0 g silver oxide until the conversion to Russig's Blue was complete. The unreacted silver oxide was filtered and washed with chloroform. The filtrate and chloroform washings were combined and stirred with 4.9 g of 4-methoxy-1-naphthol until the solution turned gray. The solution was then concentrated to 50 mL and the resulting precipitate was filtered, washed with chloroform and dried to yield 3.18 g of 1,1'-dimethoxy-3,3'-binaphthyl-4,4'-diol as a light gray solid. The structure was confirmed by NMR.

To a solution of 12.6 g of 4,4'-dimethoxy-2,2'-binaphthyl-1,1'-diol in 88 mL of dry pyridine at −20° C., under nitrogen, was added 20.56 g trifluoromethanesulfonic anhydride. The reaction mixture was allowed to warm to 0° C. and was then refrigerated for 48 hours. The mixture was diluted with ether and washed 4× with water. The ether mixture was dried over anhydrous magnesium sulfate, filtered and concentrated. The resulting crude aryl triflate was purified by column chromatography on silica gel. The resulting viscous liquid was further purified by treatment with activated charcoal and recrystallization from isopropanol to yield 17.96 g of 1,1'-dimethoxy-3,3'-binaphthyl-4,4'-ditriflate as a crystalline solid. The structure was confirmed by NMR and mass spectroscopy.

To 7.9 g of 1,1'-dimethoxy-3,3'-binaphthyl-4,4'-ditriflate in 350 mL dry dimethylformamide, under nitrogen, was added 1.464 g dichloro[1,1'-bis(diphenylphosphino)ferrocene]palladium(II), 7.9 g triethylamine and 2.1 g of 98% formic acid. The resulting mixture was heated under nitrogen at 77° C. for 20 hours. The reaction mixture was then cooled to room temperature, diluted with ethylacetate and washed 4× with water. The ethyl acetate solution was dried over anhydrous magnesium sulfate, filtered and the ethyl acetate evaporated to yield 3.40 g of a brown residue. The brown residue was purified by column chromatography on silica gel to yield 2.21 g of 1,1'-dimethoxy-3,3'-binaphthalene as a solid. The structure was confirmed by NMR and mass spectroscopy.

To a solution of 1.0 g of 1,1'-dimethoxy-3,3'-binaphthalene in 5 mL dry dimethylformamide, cooled to 0° C.-4° C., was added dropwise a solution of 1.132 g N-bromosuccinimide in 5 mL dry dimethylformamide. The resulting mixture was stirred at room temperature overnight and then poured onto ice. The resulting off-white precipitate was filtered, washed with warm water and dried to yield 1.38 g of 1,1'-dimethoxy-4,4'-dibromo-3,3'-binaphthalene as a light tan solid. NMR and mass spectroscopy confirmed the structure.

To a well stirred and cooled (−10° C.-0° C.) slurry of 1.20 g of the above binaphthalene in dry tetrahydrofuran was slowly added, under nitrogen, 2.44 mL of a 2.5 M solution of n-butyllithium in hexanes. The resulting solution was stirred at −0° C. for 45 minutes followed by the addition of 0.504 g of 1,8-naphthalic anhydride. The solution was allowed to warm to room temperature. It was then refluxed for 5 hours, quenched with water and acidified with concentrated hydrochloric acid. The resulting mixture was extracted with methylene chloride, the methylene chloride extracts were washed with water and dried over anhydrous sodium sulfate. The sodium sulfate was filtered and the methylene chloride evaporated in vacuo to yield 1.434 g of a yellow solid. The yellow solid was purified by column chromatography on silica gel to yield 0.155 g of 4,4'-(1,1'-dimethoxy-3,3'-binaphthyl)naphthalide as a tan solid. NMR and mass spectroscopy confirmed the structure.

The dimethoxy compound was converted to the dihydroxy compound by the procedure described in step 5 of Example 1 above. The crude product was recrystallized from isopropanol to yield 0.731 g of the Title Compound (12), 4,4'-(1,1'-dihydroxy-3,3'-binaphthyl)-naphthalide, as a light yellow solid, λmax=920 nm (δ=330). The structure was confirmed by NMR and mass spectroscopy.

EXAMPLE 14

Preparation of Compound (14) having the formula

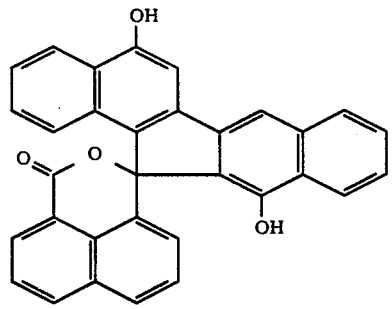

1,1'-dihydroxy-3,3'-binaphthalene was reacted with 3,3-naphthaloyl dichloride in a manner analogous to that described in Example 1, step 6. The resulting reaction mixture was then allowed to stir for three days at 72° C. followed by the addition of 4 mL of nitrobenzene. Heating was Continued at 82° C. for 18 hours. The reaction mixture was allowed to warm to room temperature and was quenched by pouring it into 200 mL of ice-water, followed by heating at 80° C. for 1¼ hours. The reaction mixture was extracted with several portions of methylene chloride, the organic extracts were combined, dried over anhydrous magnesium sulfate, filtered and concentrated in vacuo to yield 0.15 g of crude Title Compound (14). Purification was accomplished by column chromatography on silica gel to obtain 10 mg of a white solid which NMR and mass spectroscopy confirmed to be Title Compound (14), λ=774 nm (δ=2200).

The 1,1'-dihydroxy-3,3'-binaphthalene used above was prepared by converting 1,1'-dimethoxy-3,3'-binaphthalene, synthesized as in Example 13 above, to 1,1'-dihydroxy-3,3'-binaphthalene by a procedure analogous to that described in step 5 of Example 1.

EXAMPLE 15

Preparation of Compound (15) having the formula

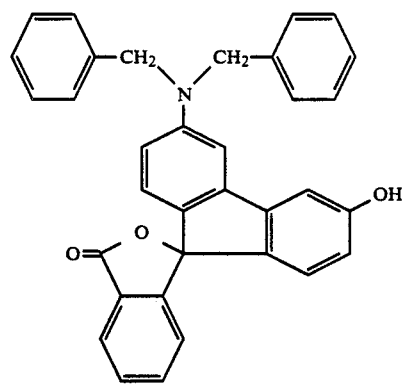

A mixture of 16 g of 3-bromoaniline, 15 g magnesium oxide and 31.8 g benzylbromide in 100 mL dry dimethylformamide was stirred for 47 hours at room temperature, under nitrogen. The precipitated magnesium salts were filtered. The filtrate was diluted with water and extracted with ether. The ether extracts were combined, washed with water and dried over anhydrous sodium sulfate. The sodium sulfate was filtered and the ether evaporated in vacuo to give a brownish solid. The brownish solid was recrystallized from isopropanol to yield 20.75 g of N,N-dibenzyl-3-bromoaniline as a white solid. The structure was confirmed by NMR.

A mixture of 3.45 g 3-bromoanisole, 0.45 g magnesium turnings and several drops of bromomethylether in 30 mL diethyl ether, under nitrogen, was stirred and refluxed for 3 hours. The solution was then allowed to cool to room temperature and a mixture of 5 g of N,N-dibenzyl-3-bromoaniline and 0.197 g bis(triphenylphosphine)nickel(II)bromide in 30 mL ether was added all at once. The resulting mixture was stirred and refluxed under nitrogen for 3¼ hours, then stirred at room temperature for 65 hours, followed by reflux for 5 hours. After cooling to room temperature the reaction mixture was quenched by adding water. The ether layer was separated, washed with water and dried over anhydrous sodium sulfate. The sodium sulfate was filtered and the ether evaporated in vacuo to give an oil. The oil was purified on a silica gel column with hexane as eluent followed by 2%, 5%, 10%, and 30% methylene chloride in hexane as eluents to yield 3.8 g of 3-N,N-dibenzylamino-3'-methoxybiphenyl as a white solid. NMR and mass spectroscopy confirmed the structure.

To a stirred mixture of 1 g phthalyl chloride and 1.47 g aluminum chloride in 15 mL 1,1,2,2-tetrachloroethane, under nitrogen and cooled to 0° C.–5° C., was added a solution of 1.90 g of 3-N,N-dibenzylamino-3'-methoxybiphenyl in 20 mL 1,1,2,2-tetrachloroethane at 0° C.–5 C over a ¼-hour period. The mixture was then stirred at 0° C.–5° C. for 15 minutes, warmed to room temperature and then stirred for 27 hours. The reaction mixture was quenched with water and extracted with methylene chloride. The methylene chloride extracts were washed with water and dried over anhydrous sodium sulfate. The sodium sulfate was filtered and the methylene chloride evaporated in vacuo. The resulting residue was purified by column chromatography on silica gel using methylene chloride as eluent to yield the methoxy phthalide as a white solid. The structure was confirmed by NMR and mass spectroscopy.

To a −5° C. solution of 1.38 g boron tribromide in 25 mL methylene chloride under nitrogen was added, dropwise, a −5° C. solution of 0.7 g of the methoxy phthalide in 20 mL methylene chloride over a ¼-hour period. The resulting green mixture was stirred at −5° C. for ¼ hour and then allowed to sit in the refrigerator overnight. The reaction was then quenched with water. The methylene chloride layer and aqueous layer were separated. The aqueous layer was washed with methylene chloride. The methylene chloride layer and washing were combined, dried over anhydrous sodium sulfate, filtered and the methylene chloride was evaporated in vacuo. The dark green solid residue was purified by chromatography on silica gel with methylene chloride and 3% methanol in methylene chloride as eluents to yield Title Compound (15) as a greenish solid, λmax=716 nm. The structure was confirmed by NMR and mass spectroscopy.

EXAMPLES 16 AND 17

Preparation of compounds (16) and (17) having the formulae

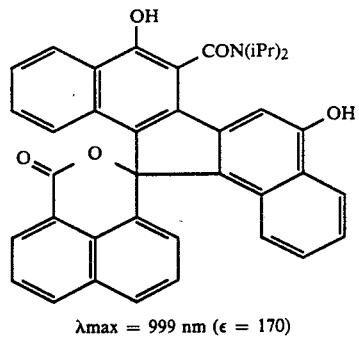

λmax = 999 nm (ε = 170)

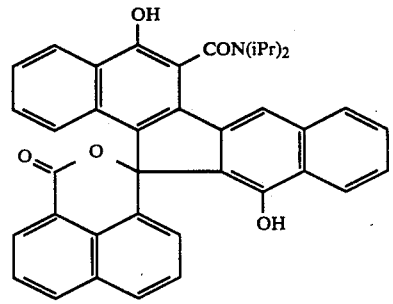

λmax = 803 nm (ε = 8,360)

Compounds (16) and (17) were prepared in a manner analogous to that for Compounds (3) and (4) in Examples 3 and 4, above. 1,1'-dihydroxy-2-(N,N-diisopropylcarbamoyl)-3,3'-binaphthalene was reacted with 3,3-naphthaloyl dichloride in the presence of aluminum chloride to yield a 12:1 mixture of Compounds (16) and (17) which were separated by column chromatography. NMR and mass spectroscopy confirmed the structures.

The biaryl, 1,1'-dihydroxy-2-(N,N-diisopropylcarbamoyl)-3,3'-binaphthalene used to prepare Compounds (16) and (17) was made by a procedure analogous to the coupling procedure set out in Example 1, above.

EXAMPLES 18 AND 19

Preparation of Compounds (18) and (19) having the following formulae

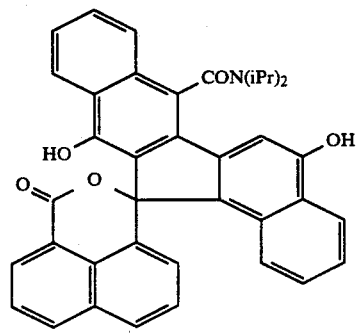

λmax = 717 nm (ε = 4790)

-continued

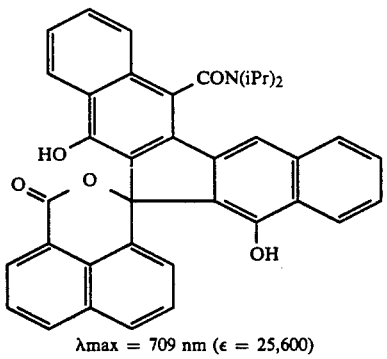

(19)

λmax = 709 nm (ε = 25,600)

Compound (18) and (19) were prepared in a manner analogous to that for Compounds (16) and (17) in Examples 16 and 17, above, except that 1,1'-dihydroxy-4-(N,N-diisopropylcarbamoyl)-3,3'-binaphthalene was used in place of 1,1'-dihydroxy-2-(N,N-diisopropylcarbamoyl)-3,3'-binaphthalene. 1,1'-dihydroxy-4-(N,N-diisopropylcarbamoyl)-3,3'-binaphthalene was reacted with 3,3'-naphthaloyl dichloride in the presence of aluminum chloride to yield a mixture of Compounds (18) and (19) which were separated by column chromatography. The respective structures were confirmed by NMR and mass spectroscopy.

EXAMPLE 20

Preparation of Compound (20) having the formula

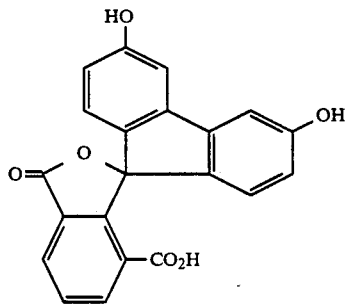

(1) A solution containing 8 g of N-bromosuccinimide in 100 mL of dimethylformamide was added dropwise, over a 90-minute period, to a solution of 9.7 g of 3,3'-dimethoxybiphenyl in 75 mL of dimethylformamide chilled in an ice-water bath. After the addition was completed, the ice-water bath was removed and the reaction mixture was stirred at room temperature overnight. The reaction mixture was then poured into 600 mL of vigorously stirred water to obtain a tan oil which separated out. The oil was dissolved in hexanes and the resulting solution was washed several times with water. The hexanes were removed to yield a tan oil which was dried in vacuo resulting in 12.6 g of 2-bromo-5,5'-dimethoxybiphenyl. The structure was confirmed by NMR and mass spectroscopy.

(2) 12.1 g of 6-bromo-3,3'-dimethoxy-biphenyl was dissolved in 100 mL of dry dimethylformamide and the resulting solution was cooled to −60° C. under nitrogen. 55 mL of 1.7 M t-butyllithium in hexanes was added over a 20-minute period. The resulting solution was transferred to another flask containing a mixture of 275 mL of ether and dry ice which effected a lot of gas evolution. The mixture was allowed to warm to room temperature over a 3-hour period during which time a white precipitate had formed. The mixture was diluted with ether and treated with dilute hydrochloric acid and water. The organic layer was separated and the solvents were removed under reduced pressure to yield a yellow oil. Hexanes were added to the oil causing a solid to precipitate out. The solids were filtered and stirred in a 60:40% ether-hexane mixture to remove impurities. The solid was filtered and dried in vacuo to yield 7.82 g of 2-carboxy-5,5'-dimethoxybiphenyl as an off-white solid. The structure was confirmed by NMR and infrared spectroscopy.

(3) 7.5 g of 2-carboxy-5,5'-dimethoxybiphenyl was dissolved in 75 mL of methanesulfonic acid to obtain a dark brown solution. The solution was stirred at room temperature for one hour, heated at 40°-50° C. for 5 hours and then cooled to room temperature. The reaction mixture was then poured onto crushed ice to form a yellow colored precipitate which was collected by filtration. The precipitate was washed with large amounts of water and then air dried to yield 6.7 g of crude 3,6-dimethoxy-9-fluorenone. Recrystallization from ethanol followed by column chromatography on silica gel using methylene chloride as the eluent yielded pure 3,6-dimethoxy-9-fluorenone. The structure was confirmed by NMR and mass spectroscopy.

(4) 8 mL of 1.5 M lithium diisopropylamide in tetrahydrofuran (hereinafter THF) was added to 35 mL of dry THF under nitrogen. The resulting solution was cooled to 105° C. using a liquid nitrogen - ether bath. To this cooled solution was added, over a 30-minute period with vigorous stirring, 1.5 g of 1,3-dicyanobenzene dissolved in 55 mL of dry THF. After the addition was complete, stirring was continued for an additional 15 minutes and a solution of 2.2 g of 3,6-dimethoxy-9-fluorenone (prepared in step 1, above) in 70 mL of THF (heat was required for dissolution) was introduced dropwise over a ≈10-minute period. The resulting thick, tan slurry was maintained between −95° to −85° C. for 90 minutes and then gradually (over a 4-hour period) brought to room temperature and was allowed to stir at room temperature overnight.

The reaction mixture was diluted with 150 mL of hexane which resulted in the formation of a tan precipitate. The precipitate was filtered, washed with THF/hexanes and then with hexanes. To the dried precipitate was then added dilute hydrochloric acid and the solution was then heated at 55°-60° C. for 4 hours.

The olive-tan precipitate which had formed was filtered, washed with water and air dried to yield 2.1 g of spiro[3,6-dimethoxyfluorene-7'-cyano-9,1'-phthalan]-3'-one.

(3) 2.0 g of spiro[3,6-dimethoxy-7'-cyano-9,1'-phthalan]-3'-one was suspended in 150 mL of methanol to which was added 10 mL of a 45% $^{wt}/_{wt}$ potassium hydroxide solution and 10 mL of water. The resulting mixture was heated at reflux for 4 hours with small quantities of 30% hydrogen peroxide added at 30 minute gintervals and then heated at 40° C. overnight.

Additional 30% hydrogen peroxide was added to the reaction mixture and reflux was resumed for 5 hours. The solvents were removed to yield a yellow, wet taffy-like material. Water was added and the aqueous mixture was extracted with 3 portions of methylene chloride. Sodium chloride was added to the aqueous solution, and the resulting mixture was cooled in an ice bath and made strongly acidic with concentrated hydrochlorine acid. The resulting off-white precipitate was filtered and then dissolved in a large volume of ethyl acetate.

Filtration of the ethyl acetate was accomplished to remove an insoluble brown residue. The ethylacetate solution was then concentrated to yield a green solid. The green solid was dissolved in hot acetone and diluted with hexanes. The off-white solid, which had formed was filtered and the filtrate was concentrated to yield 0.6 g of spiro[3,6-dimethoxy-7'-carboxy-9,1'-phthalan]-3'-one as a greenish solid.

(4) 0.5 g of spiro[3,6-dimethoxy-7'-carboxy-9,1'-phthalan]-3'-one was converted into Title Compound 20 by reaction with boron tribromide. The structure was confirmed by NMR and mass spectroscopy. When the title compound was dissolved in 1 N alkali to ensure a pH greater than the pKa of the title compound, the solution turned green (λmax=800 nm) at room temperature. However, upon heating the color intensifies, i.e., at 25° C., ε=550 (λmax=801); at 66° C., ε=1100 (λmax=801); at 80° C., ε=1300 (λmax=801).

A preferred embodiment of the bridged indicator dyes of this invention for use as infrared opacifying dyes are those represented by Formula I wherein at least one of said A or B is additionally substituted with a bulky group ortho to the bridging carbon, said bulky group being capable of exerting sufficient steric interference to effectively impede base attack at the meso carbon atom thereby imparting increased base stability to the compounds. These preferred indicator dyes may be represented by the following formula

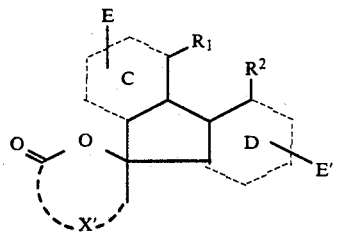

III wherein C and D represent carbocyclic aryl groups, e.g. of the benzene, naphthalene or phenanthrene series; E and E' represent an amino or hydroxy group positioned either ortho or para to the meso carbon and meta to the bridging carbon, provided that at least one of E or E' is hydroxy and preferably both are hydroxy; $R_1$ and $R_2$ represent bulky groups or hydrogen provided at least one of $R_1$ and $R_2$ is a bulky group; and X' represents the atoms necessary to complete phthalide or naphthalide and preferably X' completes naphthalide.

The amino group may be unsubstituted, mono- or disubstituted and if substituted may be substituted with such groups as those described in Formula I.

Representative bulky groups include branched alkyl groups having at least 3 carbon atoms; disubstituted amides represented by

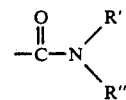

wherein R' and R", the same or different, represent branched alkyl groups having at least 3 carbon atoms, e.g. isopropyl or isobutyl, and other groups capable of exerting sufficient steric interference to impede base attack; and, disubstituted sulfonamides represented by

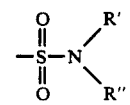

wherein R' and R" have the same meaning as above.

As in Formula I, the dyes represented in Formula III may contain additional substituents as desired which do not interfere with the function of the compounds as opacifying dyes, such as, solubilizing group(s), e.g. carboxy and sulfo groups; immobilizing group(s), e.g. long chain alkoxy groups; and/or with hydrogen bonding groups to adjust the pKa of the desired indicator dye. The additional substituents may be substituted on the C and/or D radicals and/or on the ring closing moiety.

Examples of indicator dyes with enhanced base stability include those represented by structures (3), (4), (11), (16), (17), (18), (19), (21), (22), (23) and (24), above.

As an illustration of the increased base stability of the indicator dyes of Formula III relative to other indicator dyes of this invention, the compounds of Examples 1, 3, 4, 7, and 11 were stirred in a solution of 2 N Potassium hydroxide containing 10% by weight of methanol. The absorption spectrum of these solutions was measured after 1 hour, 3 hours, 1 day, 3 days, and 10 days.

By extrapolating the measured loss in absorption for each of these solutions at the various time intervals mentioned above (assuming pseudo-first order kinetics), the half-life (t½) for those compounds which lost absorption in base was calculated and the resulting values are reported in Table II. Those compounds designated "stable" showed no appreciable absorption loss after 10 days.

A comparison of the data of Examples 1, 7 and 11 in Table II clearly reveals that as the steric bulk of either the $R_1$ or $R_2$ group is increased, the base stability of the bridged indicator dyes also increased. The compounds of Examples 3, 4 and 11 which have a —CON(iPr)$_2$ group substituted in either the $R_1$ or $R_2$ position showed no appreciable loss in absorption in base after 10 days, indicating the N,N'-diisopropyl amide group is effective in preventing base attack at the meso carbon.

TABLE II

| Structure | R₁ | R₂ | Experimental Example | t½ |
|---|---|---|---|---|
| | CH₃ | H | 1 | 33 days |
| | CONHt-Bu | H | 7 | 77 days |
| | CON(iPr)₂ | H | 11 | stable |
| | H | CON(iPr)₂ | 3 | stable |
| | H | CON(iPr)₂ | 4 | stable |

It has unexpectedly been found that when the compounds of Formula I are such that said A and said B are each selected from a carbocyclic aryl radical containing as said substituent a hydroxy group and both of said hydroxy groups are positioned ortho to the meso carbon and meta to the bridging carbon, a solution of these compounds in aqueous hydroxide possess a narrower principal absorption bandwidth, a hypsochromic shift (shift to shorter wavelengths) and an unexpectedly large increase in the molar absorptivity, ($\epsilon$), of the indicator dye relative to the analogous indicator dye which has both hydroxy groups in the position para to the meso carbon and meta to the bridging carbon and also, relative to the two analogous indicator dyes each of which have one hydroxy group ortho and one hydroxy group para to the meso carbon.

Compounds (16), (17), (18) and (19), shown below, illustrate the above. The λmax, ($\epsilon$) and absorption spectrum for each compound were measured in a 1 N hydroxide solution.

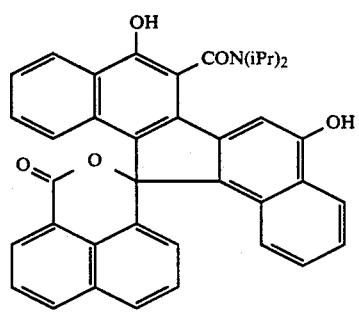

(16)

λmax = 999 nm ($\epsilon$ = 170)

-continued

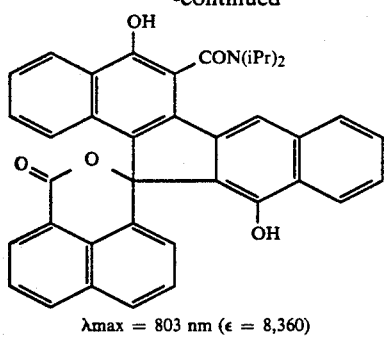
(17)
λmax = 803 nm (ε = 8,360)

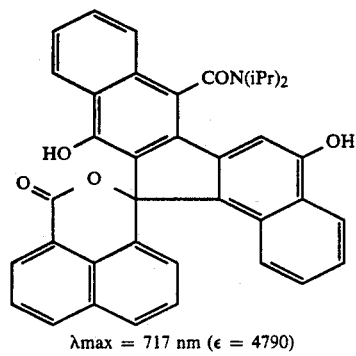
(18)
λmax = 717 nm (ε = 4790)

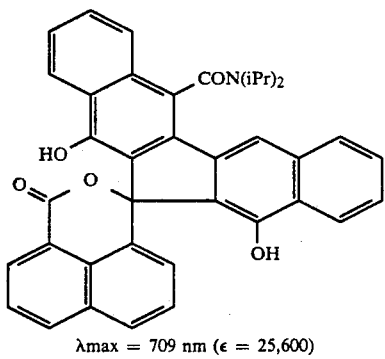
(19)
λmax = 709 nm (ε = 25,600)

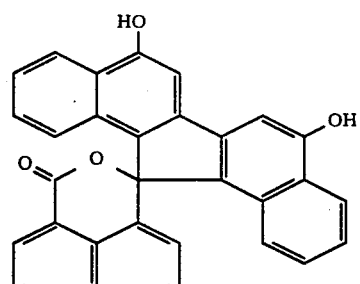
(13)
λmax = 920 nm (ε = 330)

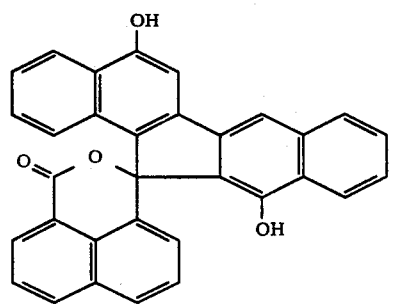
(14)
λmax = 774 nm (ε = 2200)

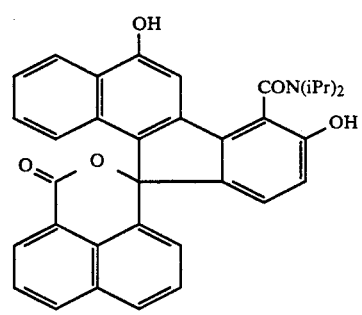
(3)
λmax = 728 nm (ε = 930)

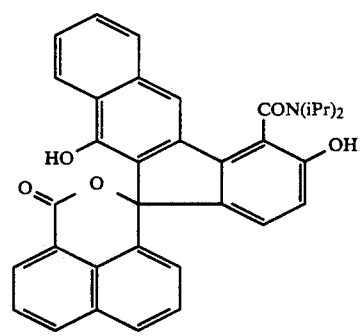
(4)
λmax = 664 nm (ε = 10,100)

Figure 10:
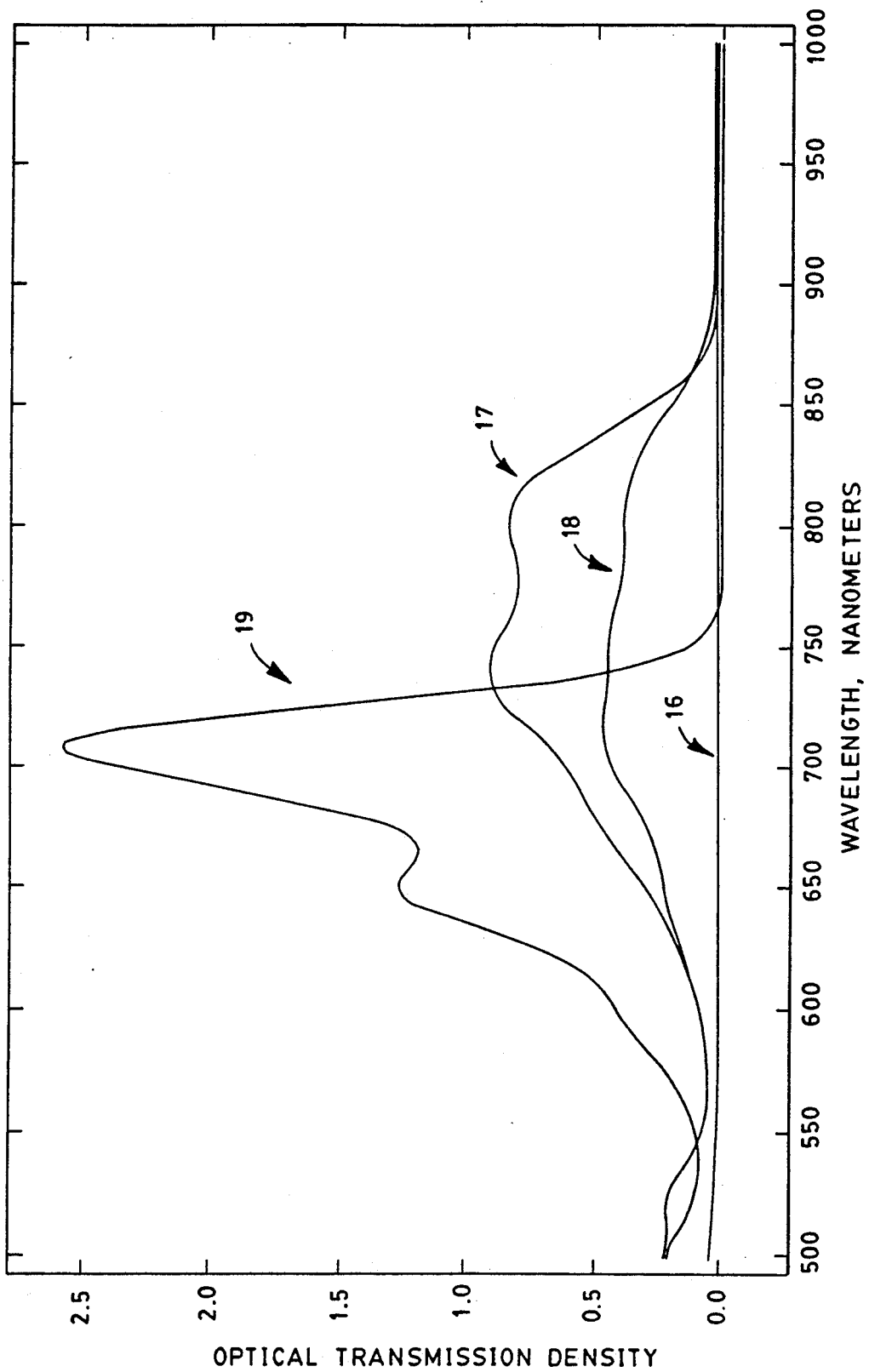
FIG. 10 graphically illustrates the spectral absorption characteristics of four indicator dyes of the present invention at the same concentrations in base over the wavelength range of 500 to 1000 nm.

Curves 16, 17, 18 and 19 in FIG. 10 represent, respectively, the optical transmission density, i.e., the absorbance of compounds (16), (17), (18) and (19) measured over the wavelength range of 500 to 1000 nm at the same concentrations. A comparison of the above four indicator dyes clearly shows a hypsochromic shift, a substantial increase in the molar absorptivity and a bandwidth narrowing when comparing the ortho, ortho hydroxy substituted dye (19) with the para, ortho hydroxy substituted (17) and the ortho, para hydroxy substituted (18) dyes. This bandwidth narrowing, hypsochromic shift and increase in molar absorptivity is even more pronounced when comparing the ortho, ortho (19) with the para, para (16) hydroxy substituted dye.

Figure 8:
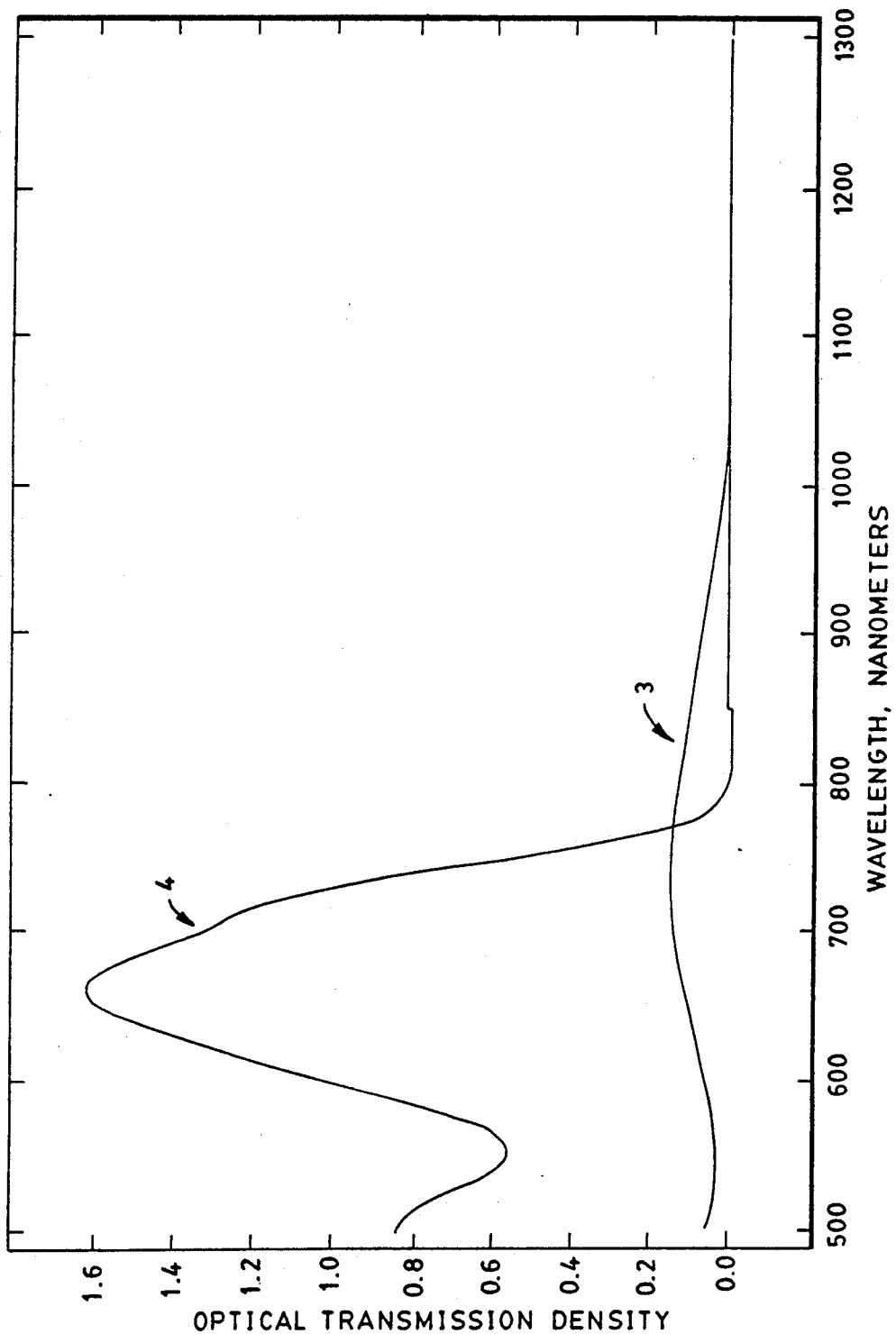
FIGS. 8 and 9 each contain graphic illustrations of the spectral absorption characteristics of two indicator dyes of the present invention in an aqueous alkaline solution.

As demonstrated by the above data, the para, ortho hydroxy substituted dye (17) and the ortho, para hydroxy substituted dye (18) relative to the analogous para, para hydroxy substituted dye (16) show a hypsochromic shift, bandwidth narrowing and increase in molar absorptivity. In addition to the above compounds, this is further illustrated by compounds (13) and (14) and compounds (3) and (4), as follows:

FIG. 8 is a graphic representation of the spectral absorption characteristics of compounds (3) and (4) at the same concentrations in aqueous base. Curves 3 and 4 in FIG. 8 represent, respectively, the optical transmission density, i.e., the absorbance of compounds (3) and (4) over the wavelength range of 500 nm to 1300 nm. A comparison of curves 3 and 4 clearly shows a narrowing of the principal absorption bandwidth for compound (4), having one hydroxy group para and the other hydroxy group ortho to the meso carbon relative to that for compound (3) which has both hydroxy groups positioned para to the meso carbon. A similar comparison of the absorption spectra of compounds (13) and (14) also shows a narrowing of the principal absorption bandwidth for compound (14) relative that for compound (13).

However, a comparison of compounds (5) and (6) and (7) and (8) reveals that not all the compounds of Formula I exhibit the same phenomena, i.e., narrower bandwidth, hypsochromic shift and dramatic increase in ($\epsilon$) when comparing the dye with one hydroxy group ortho to the meso carbon and the other hydroxy group para to the meso carbo with the analogous dye having both hydroxy groups para to the meso carbon. Specifically, the following was observed:

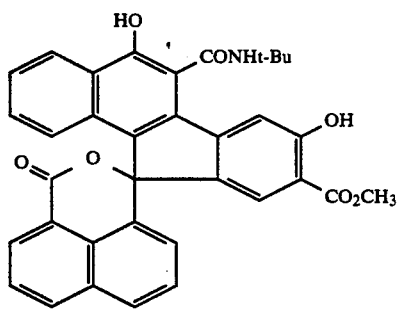

$\lambda$max = 730 nm ($\epsilon$ = 1528)     (5)

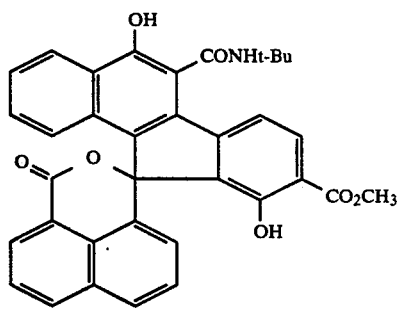

$\lambda$max = 731 nm ($\epsilon$ = 396)     (6)

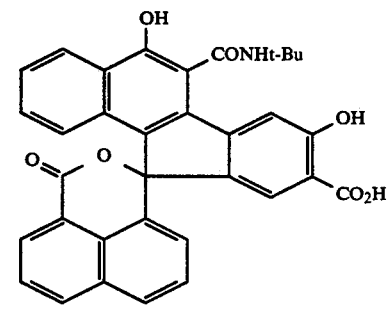

$\lambda$max = 765 nm ($\epsilon$ = 1670)     (7)

-continued

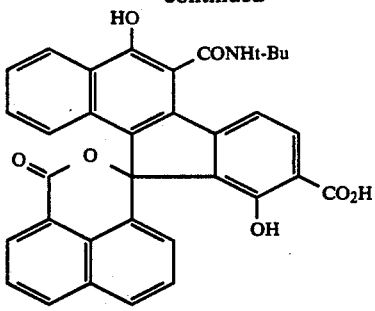

$\lambda$max = 745 nm ($\epsilon$ = 450)     (8)

Figure 9:
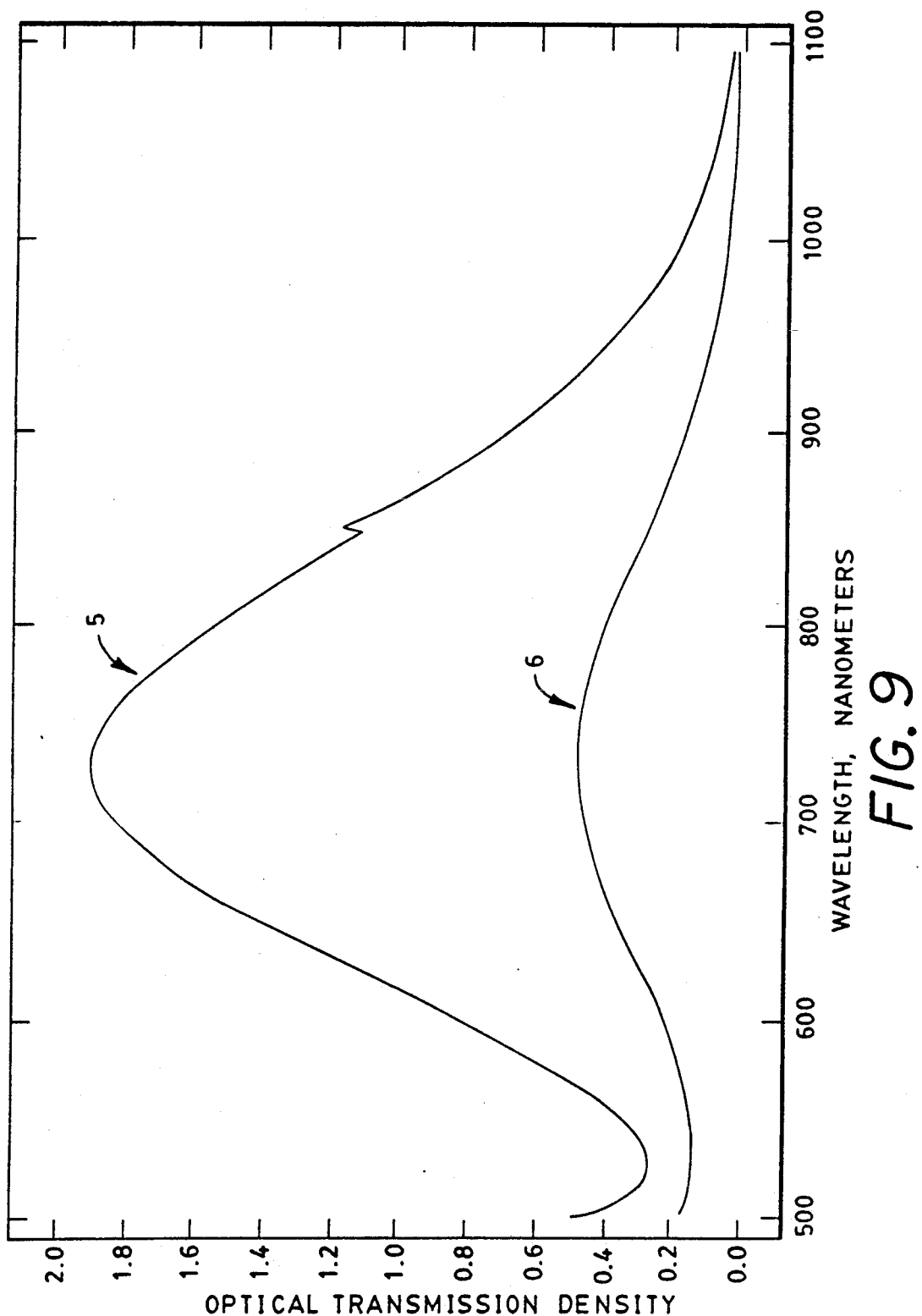

FIG. 9 is a graphic representation of the spectral absorption characteristics of compounds (5) and (6) at the same concentrations in aqueous base. Curves 5 and 6 in FIG. 9 represent, respectively, the optical transmission density, i.e., the absorbance of compounds (5) and (6) at the same concentrations over the wavelength range of 500 nm to 1100 nm. A comparison of curves 5 and 6 shows that the principal absorption bandwidths for both are substantially the same. A comparison of the absorption spectra of compounds (7) and (8) measured in aqueous alkali at the same concentrations over the same wavelength range also showed the two bandwidths as being substantially the same.

In the use of the compounds of this invention as opacifying dyes, a high molar absorptivity in the region of the spectrum where protection is required and base stability of the indicator dyes are desired characteristics. Based on these, a particularly preferred embodiment of the dyes of this invention, for use as opacifiers, are those of Formula III, wherein both of said E and said E' are hydroxy groups and both of said E and E' are ortho to the meso carbon. Another preferred embodiment of the dyes of this invention, particularly when a $\lambda$max in the infrared is desired, are those of Formula III, wherein both of said E and E' are hydroxy groups and one of said E and E' is para to the meso carbon and the other of said E or E' is ortho to the meso carbon atom, provided further that said pH-sensitive bridged indicator dye shows a narrowing of the principal absorption bandwidth, a hypsochromic shift of $\lambda$max and an increase in molar absorptivity relative to the analogous pH-sensitive indicator dye in which both hydroxy groups are para to the meso carbon atom.

It should be noted that many of the indicator dyes of this invention have absorption in the visible region of the spectrum as well as absorption in the infrared region. Those indicator dyes having absorption may also be useful as opacifying dyes in the visible region of the spectrum.

As noted above, the present invention is particularly adapted for facilitating processing outside a camera of diffusion transfer units which are maintained as a permanent integral laminate after processing, the final transfer image being viewed through one face of the laminate. In such film units a light-reflecting layer is disposed between the developed photosensitive layers and the layer carrying the transfer dye image. These essential layers preferably are confined between a pair of dimensionally stable outer supports, at least one of which is transparent to permit viewing of the transfer dye image by reflection against the background, preferably white, provided by the reflecting layer.

Image dye-providing materials which may be employed generally may be characterized as either (1) initially soluble or diffusible in the processing composition but are selectively rendered non-diffusible in an imagewise pattern as a function of development; or (2) initially insoluble or non-diffusible in the processing composition but which are selectively rendered diffusible or provide a diffusible product in an imagewise distribution as a function of development. These materials may be complete dyes or dye intermediates, e.g., color couplers. The requisite differential in mobility or solubility may, for example, be obtained by a chemical action such as a redox reaction, a coupling reaction or a silver ion assisted cleavage reaction.

Examples of initially soluble or diffusible materials and their application in color diffusion transfer processes are disclosed, for example, in U.S. Pat. Nos. 2,968,554; 2,983,606; 3,087,817; 3,185,567; 3,230,082; 3,345,163; and 3,443,943. Examples of initially non-diffusible materials and their use in color transfer systems are disclosed in U.S. Pat. Nos. 3,185,567; 3,443,939; 3,443,940; 3,227,550; 3,227,552 and 4,076,529. Both types of image dye-providing substances and film units useful therewith also are discussed in the aforementioned U.S. Pat. No. 3,647,437 to which reference may be made.

A particularly useful system for forming color images by diffusion transfer is that described in U.S. Pat. No. 2,983,606, employing dye developers (dyes which are also silver halide developing agents) as the image dye-providing materials. In such systems, a photosensitive element comprising at least one silver halide layer having a dye developer associated therewith (in the same or in an adjacent layer) is developed by applying an aqueous alkaline processing composition. Development of exposed silver halide results in oxidation of the dye developer to provide an oxidation product which is appreciably less diffusible than the unreacted dye developer, thereby providing an imagewise distribution of diffusible dye developer in terms of unexposed areas of the silver halide layer, which imagewise distribution is then transferred, at least in part, by diffusion, to a dyeable stratum to impart thereto a positive dye transfer image.

Another system that is particularly useful for forming color images by diffusion transfer is that described in U.S. Pat. No. 4,740,448, which uses the aforementioned dye developer chemistry to form at least one color record and the image dye-releasing thiazolidine chemistry of U.S. Pat. No. 3,719,489 to form at least one of the other color records.

In such color diffusion transfer systems, color transfer images are obtained by exposing a photosensitive element, sometimes referred to as a "negative component", comprising at least a light-sensitive layer, e.g., a gelatino silver halide emulsion layer, having an image dye-providing material associated therewith in the same or in an adjacent layer, to form a developable image; developing this exposed element with a processing composition to form an imagewise distribution of a diffusible image dye-providing material; and transferring this imagewise distribution, at least in part, by diffusion, to a superposed image-receiving layer, sometimes referred to as a "positive component", comprising at least a dyeable stratum to provide a color transfer image. The negative and positive components initially may be carried on separate supports which are brought together during processing and thereafter retained together as the final integral negative-positive reflection print, or they may initially comprise a unitary structure, e.g., integral negative-positive film units of the type described in aforementioned U.S. Pat. No. 3,415,644 wherein the negative and positive components are physically retained together in superposed relationship prior to, during and after image formation. (Procedures for forming such film units wherein the positive and negative components are temporarily laminated together prior to exposure are described, for example, in U.S. Pat. No. 3,652,281 to Albert J. Bachelder and Frederick J. Binda and in U.S. Pat. No. 3,652,282 to Edwin H. Land, both issued Mar. 28, 1972.) In either instance, the positive component is not removed from the negative component for viewing purposes. These components may be laminated together or otherwise secured together in physical juxtaposition.

Film units intended to provide multicolor images comprise two or more selectively sensitized silver halide layers each having associated therewith an appropriate image dye-providing material. The present invention is particularly useful for photographic films wherein at least one of the silver halide layers is spectrally sensitized to the near-infrared. The most commonly employed negative components for forming multicolor images are of the tripack structure and contain three spectrally sensitized silver halide layers each having associated therewith in the same or in a contiguous layer a yellow, a magenta and a cyan image dye-providing material. Interlayers or spacer layers may be provided between the respective silver halide layers and associated image dye-providing materials or between other layers. Indeed, a light-reflecting spacer layer disposed between a silver halide layer and the associated layer of image dye-providing material may be used to increase effective film speed as a result of the reflection of light back to the silver halide. Particularly suitable light-reflecting spacer layers comprise a light-reflecting pigment dispersed with inert polymeric particles which are substantially non-swelling in alkali and substantially non-film-forming. Such layers form the subject matter of published European Patent Application No. 0066341 published Dec. 8, 1982.

In addition to the aforementioned layers, such film units further include means for providing a reflecting layer between the dyeable stratum and the negative component in order to mask effectively the silver image or images formed as a function of development of the silver halide layer or layers and also to mask image dye-providing material which is not transferred, thereby providing a background, preferably white, for viewing the color image formed in the dyeable stratum, without separation, by reflected light. Preferably, this reflecting layer is provided by including the reflecting agent in the processing composition. The dye transfer image is then viewable against the reflecting layer through a dimensionally stable protective layer or support. As noted above, most preferably another dimensionally stable layer or support is positioned on the opposed surface of the essential layers so that the aforementioned essential layers are between a pair of dimensionally stable layers or support members, one of which is transparent to permit viewing therethrough of the color transfer image. The requisite processing composition may be applied to the photosensitive element, e.g. by coating, dipping, spraying or preferably by the use of a rupturable container or pod such as disclosed in U.S. Pat. No. 2,543,181. The container or pod is so positioned as to be capable, upon application of pressure, to release its contents for development of the exposed film unit, e.g., by distributing the processing composition in a substantially uniform layer between the negative and positive components.

The dye developers (or other image dye-providing substances) are preferably selected for their ability to provide colors that are useful in carrying out subtractive color photography, that is, the previously mentioned cyan, magenta and yellow. They may be incorporated in the respective silver halide emulsion or, in the preferred embodiment, in a separate layer behind the respective silver halide emulsion. Thus a dye developer may, for example, be in a coating or layer behind the respective silver halide emulsion and such a layer of dye developer may be applied by use of a coating solution containing the respective dye developer distributed, in a concentration calculated to give the desired coverage of dye developer per unit area, in a film-forming natural, or synthetic polymer, for example, gelatin, polyvinyl alcohol, and the like, adapted to be permeated by the processing composition.

Dye developers, as noted above, are compounds which contain the chromophoric system of a dye and also a silver halide developing function. By "a silver halide developing function" is meant a grouping adapted to develop exposed silver halide. A preferred silver halide developing function is a hydroquinonyl group. Other suitable developing functions include orthodihydroxyphenyl and ortho- and para-amino substituted hydroxyphenyl groups. In general, the development function includes a benzenoid developing function, that is, an aromatic developing group which forms a quinoid or quinone substance when oxidized.

The image-receiving layer may comprise any of the materials known in the art, such as polyvinyl alcohol, gelatin, etc., preferably containing a mordant for the transferred image dye(s). If the color of the transferred image dye(s) is affected by changes in pH, the pH of the image layer may be adjusted to provide a pH affording the desired color.

In the various color diffusion transfer systems which have previously been described and which employ an aqueous alkaline processing fluid, it is well known to employ an acid-reacting reagent in a layer of the film unit to lower the environmental pH following substantial dye transfer in order to increase the image stability and/or to adjust the pH from the first pH at which the image dyes are diffusible to a second (lower) pH at which they are not. For example, the previously mentioned U.S. Pat. No. 3,415,644 discloses systems wherein the desired pH reduction may be effected by providing a polymeric acid layer adjacent the dyeable stratum. These polymeric acids may be polymers which contain acid groups, e.g., carboxylic acid and sulfonic acid groups, which are capable of forming salts with alkali; or potentially acid-yielding groups such as anhydrides or lactones. Preferably the acid polymer contains free carboxyl groups. Alternatively, the acid-reacting reagent may be in a layer adjacent the silver halide most distant from the image-receiving layer, as disclosed in U.S. Pat. No. 3,573,043 issued Mar. 30, 1971 to Edwin H. Land. Another system for providing an acid-reacting reagent is disclosed in U.S. Pat. No. 3,576,625 issued Apr. 27, 1971 to Edwin H. Land.

An inert interlayer or spacer layer may be used in association with the polymeric acid layer to control or "time" the pH reduction so that it is not premature and interfere with the development process. Suitable spacer or "timing" layers useful for this purpose are described with particularity in U.S. Pat. Nos. 3,362,819; 3,419,389; 3,421,893; 3,455,686; and 3,575,701.

As is now well known and illustrated, for example, in the previously cited patents, the liquid processing composition referred to for effecting multicolor diffusion transfer processes comprises at least an aqueous solution of an alkaline material and possesses a pH of at least 12. Preferably, the alkaline material employed in the subject invention is an alkali metal hydroxide.

The processing composition also preferably includes a viscosity-imparting reagent constituting a film-forming material of the type which, when the composition is spread and dried, forms a relatively firm and relatively stable film. This reagent may be a cellulosic polymer, for example, hydroxyethyl cellulose or sodium carboxymethyl cellulose; an oxime polymer, for example, polydiacetone acrylamide oxime; or other alkali-stable high molecular weight polymer. The viscosity-imparting reagent is preferably contained in the processing composition in such suitable quantities as to impart to the composition a viscosity in excess of 100 cps. at a temperature of approximately 24° C. and preferably in the order of 100,000 cps. to 200,000 cps. at that temperature.

As mentioned previously, at least one and generally two light-absorbing pH-sensitive optical filter agents which absorb in the visible region of the spectrum are used in combination with the subject bridged indicator dyes to provide further protection throughout the entire exposable spectrum. Usually an alkyl substituted phenanthrol/o-carboxynaphthol phthalein is used to provide protection in the longer wavelength region of the visible spectrum. Preferred alkyl substituted phenanthrol/o-carboxynaphthol phthaleins are those forming the subject matter of U.S. Pat. No. 4,891,298. Additionally, a light-absorbing pH-sensitive optical filter agent which absorbs in the shorter wavelength visible is also employed, usually, an indole phthalein. As used herein, the term "indole phthalein" is intended to include both 3,3-di(indol-3-yl) phthalides and 3,3-di(indol-3-yl) naphthalides such as the phthaleins disclosed in the aforementioned U.S. Pat. No. 3,702,244. Preferred indole phthaleins are those forming the subject matter of U.S. Pat. No. 4,615,966.

The pH-sensitive bridged indicator dyes of this invention employed as the light-absorbing optical filter agents may be positioned initially in a layer of the film unit, e.g. in a layer between the image-receiving and next adjacent photosensitive layer through which photo-exposure is effected provided it is incorporated under conditions, i.e. at a pH such that it will not absorb radiation intended to selectively expose the photosensitive element to form a latent image therein. For example, the optical filter agent may be in a layer coated over either the image-receiving layer or the next adjacent photosensitive layer and should remain substantially non-light absorbing until a processing composition is applied providing a pH at which the indicator dye is capable of being rapidly converted to its light absorbing form to provide light protection once the selectively exposed film unit is exposed to ambient light. In the preferred embodiment, the indicator dyes are initially contained in the processing composition in their colored form together with the light-reflecting material, e.g., titanium dioxide. If the given indicator dye exhibits instability when stored for a period of time within a pod containing the processing composition, such dye may be used by employing a double-compartmented rupturable pod or two associated rupturable pods, such that the dye is stored separate from, e.g., the alkali, and the complete processing composition containing said dye is constituted at the time of use, in accordance with techniques well understood in the art.

The concentration of bridged indicator dye is selected to provide the optical transmission density required, in combination with the other layers intermediate the silver halide emulsion layer(s) and the incident radiation, to prevent non-imagewise exposure, i.e., fogging by incident actinic light during performance of the particular photographic process. The transmission density and the concentration of bridged indicator dye necessary to provide the requisite protection from incident light may be readily determined for any photographic process by routine experimentation, as a function of film speed or sensitivity, thickness of opacification layer, processing time, anticipated incident light intensity, etc., as described in said U.S. Pat. No. 3,647,437. It will be recognized that a particular transmission density may not be required for all portions of the spectrum, lesser density being sufficient in wavelength regions corresponding to lesser sensitivities of the particular photosensitive material. As indicated above, it will be recognized that a mixture of opacifying dyes may be used to obtain absorption in all critical areas of the visible and near infrared spectrum for which the silver halide emulsions being used are exposable.

Where the light-absorbing optical filter agent is present in the processing composition, it is advantageous to utilize an image-receiving component having a surface layer adapted to decolorize the optical filter agent adjacent the interface between said component and the layer of processing composition. Suitable decolorizing layers are described in U.S. Pat. No. 4,298,674 of Edwin H. Land, Leon D. Cerankowski and Neil C. Mattucci, in U.S. Pat. No. 4,294,907 of Irena Bronstein-Bonte, Edward P. Lindholm and Lloyd D. Taylor and in U.S. Pat. 4,367,277 of Charles K. Chiklis and Neil C. Mattucci.

As an illustration of the photographic utility of the indicator dyes of this invention, photographic film units adapted to the provision of a permanent photographic laminate were prepared as described in the following examples.

EXAMPLE 21

A multicolor photosensitive element of the type described in U.S. Pat. No. 4,740,448 issued to Peter O. Kliem was prepared. The photosensitive element comprised three photosensitive emulsion layers, a green-sensitive silver halide emulsion which controlled the yellow dye density, a red-sensitive silver halide emulsion which controlled the magenta dye density and an infrared sensitive silver halide emulsion which controlled the cyan dye density. The image-receiving element comprised a 2.7 mil polyester film base, including a small amount of an anti-light piping dye, upon which there were coated in succession:

1. An image-receiving layer of a 2:1 blend of a mordant polymer and gelatin, coated at a coverage of about 200 mg/ft$^2$. The mordant polymer was a soluble copolymer comprised of vinylbenzyltrimethylammonium chloride (VBT) and vinylbenzyl dimethyldodecylammonium chloride (VBD) at a ratio of VBT/VBD of 15/1; and 2. A clearing layer coated at a coverage of about 100 mg/ft$^2$ comprising 1 part of Igepal CO-997 (nonylphenoxyethylene oxide ethanol) and 1 part of polyvinylpyrrolidone K-120.

The photosensitive element was placed in a superposed relationship with the image receiving element with their respective supports outermost and a rupturable container retaining an aqueous alkaline processing composition was fixedly mounted at the leading edge of the superposed elements, by pressure-sensitive tapes to make a film unit, so that, upon application of compressive force to the container to rupture the marginal seal of the container, the contents thereof would be distributed between the superposed elements.

the aqueous alkaline processing composition comprised:

| | |
|---|---|
| Water | 40.080 g |
| 1-(4'-hydroxyphenyl)-5-mercaptotetrazole | 0.020 g |
| Titanium dioxide | 47.774 g |
| 2-Methylimidazole | 0.484 g |
| Zonyl FSN | 0.194 g |
| Colloidal silica | 0.460 g |
| Poly(diacetone acrylamide)oxime | 0.661 g |
| Hypoxanthene | 0.654 g |
| Dow 620 carboxylated 67/33 styrene/butadiene latex | 1.470 g |
| Transexamic acid | 0.199 g |
| Potassium hydroxide | 5.733 g |
| 6-methyluracil | 0.407 g |
| n-butyl-2-picolinium bromide | 1.226 g |
| 3-(7-n-hexadecylsulfonamidoindol-3-yl)-(6-dimethylsulfamoylindol-3-yl)naphthalide (Opacifying Dye 1) | 0.300 g |
| 3-(4'-hydroxy-3'-methyl-1'-phenanthryl)-3-(3"-carboxy-4"-hydroxy-7"-n-docosanyloxy-1"'-naphthyl)naphthalide (Opacifying Dye 2) | 2.140 g |
| Bridged Indicator dye of Ex. 1 (Opacifying Dye 3) | 3.000 g |

Opacifying dye 1, i.e., 3-(7-n-hexadecylsulfonamidoindol-3-yl)-(6-dimethylsulfamoylindol-3-yl) naphthalide used in the processing composition has the structural formula:

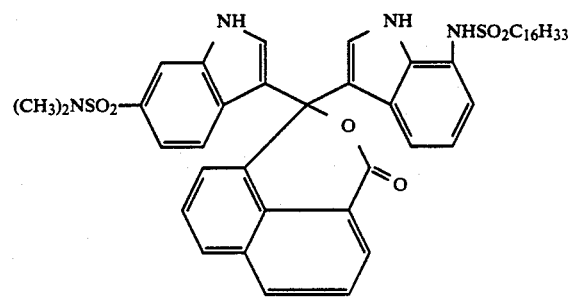

Opacifying dye 2, i.e., 3-(4'-hydroxy-3'-methyl-1'-phenanthryl)-3-(3"-carboxy -4"-hydroxy-7"-n-docosanyloxy-1-"-naphthyl)naphthalide. used in the processing composition has the structural formula:

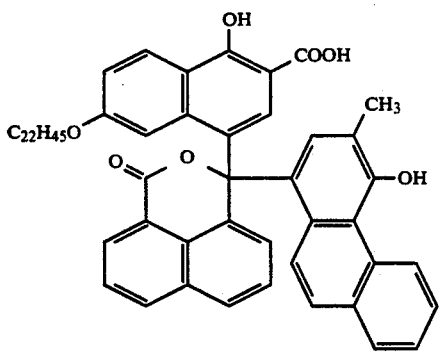

The adsorption spectrum of the processing composition containing opacifying dyes 1 and 2 but omitting the opacifying dye of this invention, is graphically illustrated by curve A in FIG. 1. The absorption was measured after removal of the titania, at a pH substantially above the pKa of each of the dyes. As can be seen from curve A, opacifying dyes 1 and 2 are useful for filtering out radiation in the visible region.

EXAMPLE 22

A second film unit was prepared in a similar manner as above, except that the bridged indicator dye of Example 2 was substituted (in the same quantity) in the processing composition for the bridged indicator dye of Example 1, and 6.136 g of potassium hydroxide was used instead of 5.733 g. The image receiving element comprised a 2.7 mil polyester film base, including a small amount of an anti-light piping dye, upon which there were coated in succession:

1. An image-receiving layer coated at a coverage about 300 mg/ft$^2$ of a graft latex comprised of vinylbenzyl triethylammonium chloride (VBT) on polyvinyl alcohol (PVA) at a ratio of VBT/PVA of 1/1; and 2. A clearing layer coated at a coverage of about 120 mg/ft$^2$ comprising 1 part Igepal CO-997 (nonylphenoxyethylene oxide ethanol), 1 part of a 1.0/1.0/0.1/0.1 tetrapolymer of methacrylic acid/diacetone acrylamide/butylacrylate/styrene and 0.3 part of polyvinylpyrrolidone.

Each of the film units was photoexposed through the image receiving element using an exposure of two meter-candle-seconds (white light) through a 0–3.0 O.D. continuous carbon wedge. The processing composition was distributed at room temperature between the elements of the film unit by passing the film unit through a motorized roller assembly. Immediately the processed film unit was placed in a water bath with a heat mirror and a type 5900 blue filter (Mooney Precision Glass) placed between the water bath containing the film unit and a second water bath. The processed film unit was kept in the water bath ~5 inches from a 10,000 ft candle (650 w) tungsten lamp for 30 seconds. The water baths and heat mirror aid in cooling the system in order to inhibit thermal fogging of the image. The blue filter acts to filter the white light to better mimic sunlight.

The test multicolor images prepared in the manner detailed above were compared to control transfer images prepared identically with the exception that the processing composition did not contain an optical filter agent of this invention for absorbing in the near infrared region. The Dmax values measured for the transferred images are set forth in the Table below.

|  | Dmax | | |
|---|---|---|---|
|  | Red (820 nm) | Green (720 nm) | Blue (640 nm) |
| Example 21 | 1.20 | 1.60 | 1.68 |
| Control | 0.39 | 1.87 | 1.66 |
| Example 22 | 0.61 | 0.91 | 0.91 |
| Control | 0.21 | 0.28 | 0.98 |

The above comparisons clearly reveal the effectiveness of the optical filter agents in preventing post-exposure fogging during processing in the presence of infrared light, as reflected by the maximum densities obtained.

To further illustrate the present invention, the optical transmission densities of the compounds of Examples 1, 2, 5, 9, 11, and 13 at the concentrations of $2.8 \times 10^{-4}$ M, $7.88 \times 10^{-4}$ M, $1.23 \times 10^{-3}$ M, $1.32 \times 10^{-4}$ M, $1.05 \times 10^{-4}$ M and $4.10 \times 10^{-4}$ M, respectively, in 1 N aqueous hydroxide were measured spectrophotometrically over the wavelength range of 500 to 1000 (the compound of Example 13 was measured over the range of 600 to 1300 nm). The resulting absorption curves designated curves B, C, D, E, F and G respectively are shown in FIGS. 2–7.

As can be seen from reference to FIGS. 2 through 7, the bridged phthaleins of the present invention absorb radiation in the near infrared region of the spectrum.

It will be understood that this invention is applicable to a wide variety of photographic processes employing any of various image-providing materials and that the transfer image may be in silver or in dye. Since such processes are now well known, it is not necessary to describe them in detail.

What is claimed is:

1. In a photographic film unit adapted for forming a transfer image viewable as a reflection print including a negative component comprising a photosensitive silver halide emulsion carried on a support; a positive component comprising an image-receiving layer carried on a transparent support; an acid-reacting layer disposed in at least one of said negative and positive components; and an aqueous alkaline processing composition comprising a light-reflecting pigment and at least one light-absorbing, pH-sensitive optical filter agent releasably contained in a rupturable container positioned to release said composition for distribution between said negative and said positive components, the combination of said light-reflecting pigment and said optical filter agent being effective to prevent further exposure of said photosensitive emulsion during processing in the presence of radiation absorbed by said optical filter agent and actinic to said emulsion, said light-reflecting pigment providing a layer after development which is effective to mask said photosensitive layer and provide a background for viewing the transfer image by reflected light;

the improvement which comprises employing as said light-absorbing pH-sensitive optical filter agent, a pH-sensitive bridged indicator dye of the formula

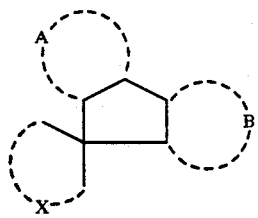

wherein A and B are selected from a first and second carbocyclic aryl radical, each possessing as a substituent an amino or hydroxy group positioned ortho or para to the meso carbon and meta to the bridging carbon, provided further that at least one of said A or B contains as said substituent a hydroxy group and X represents the atoms necessary to complete a phenolate, carboxylate or sulfinate ester ring closing moiety; provided further that when X represents the atoms necessary to complete a phthalide or sulfinate ester ring closing moeity, the phthalide or sulfinate ester moiety is not substituted in the 7'-position with a group which exerts a steric influence such that the lactone or sulfone, at a pH at or above its pKa, remains closed at room temperature.

2. A photographic film unit as defined in claim 1 wherein X represents a phthalide or naphthalide ring closing moiety.

3. A photographic film unit as defined in claim 1 wherein said A and said B are selected from said first and second carbocyclic aryl radicals each possessing as said substituent a hydroxy group.

4. A photographic film unit as defined in claim 1 wherein said pH-sensitive bridged indicator dye is represented by the formula

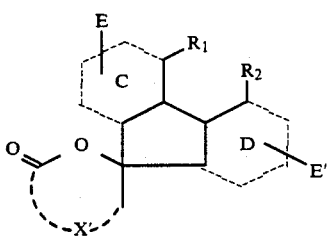

wherein C and D represent carbocyclic aryl groups; E and E' represent an unsubstituted, mono-substituted or disubstituted amino group or a hydroxy group positioned either ortho or para to the meso carbon and meta to the bridging carbon, provided that at least one of E or E' is hydroxy; $R_1$ and $R_2$ represent bulky groups or hydrogen, provided at least one of said $R_1$ and $R_2$ is a bulky group; and X' represents the atoms necessary to complete phthalide or naphthalide.

5. A photographic film unit as defined in claim 4 wherein said E and said E' are each hydroxy.

6. A photographic film unit as defined in claim 5 wherein one of said E and said E' is positioned ortho to the meso carbon and meta to the bridging carbon and the other of said E and E' is positioned para to the meso carbon and meta to the bridging carbon.

7. A photographic film unit as defined in claim 6 further providing that said pH-sensitive bridged indicator dye shows a narrowing of the principal absorption bandwidth, a hypsochromic shift of λmax and an increase in molar absorptivity relative to the analogous pH-sensitive indicator dye which has both hydroxy groups para to the meso carbon.

8. A photographic film unit as defined in claim 5 wherein both of said E and E' are positioned ortho to the meso carbon and meta to the bridging carbon.

9. A photographic film unit as defined in claim 4 wherein one of said $R_1$ or $R_2$ is a bulky group and the other of said $R_1$ or $R_2$ is hydrogen.

10. A photographic film unit as defined in claim 9 wherein said bulky group is a substituted amide represented by

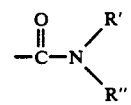

wherein R' and R" are branched alkyl groups.

11. A photographic film unit as defined in claim 9 wherein said bulky group is a substituted sulfonamide represented by

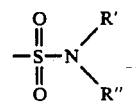

wherein R' and R" are branched alkyl groups.

12. A photographic film unit as defined in claim 1 wherein said processing composition additionally includes a viscosity imparting reagent.

13. A photographic film unit as defined in claim 1 wherein said light-reflecting pigment is titanium dioxide.

14. A photographic film unit as defined in claim 1 wherein said processing composition includes a light-absorbing, pH-sensitive alkyl substituted phenanthrol-/o-carboxynaphthol phthalein optical filter agent.

15. A photographic film unit as defined in claim 1 wherein said processing composition includes a light-absorbing indole phthalein optical filter agent.

16. A photographic film unit as defined in claim 4 wherein said pH-sensitive bridged indicator dye is represented by the formula

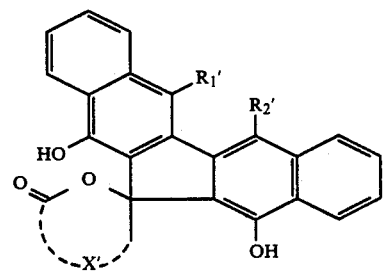

wherein $R_1'$ and $R_2'$ represent hydrogen or —CON(iPr)$_2$ provided at least one of $R_1'$ and $R_2'$ is —CON(iPr)$_2$.

17. A photographic film unit as defined in claim 4 wherein said pH-sensitive indicator dye is represented by the formula

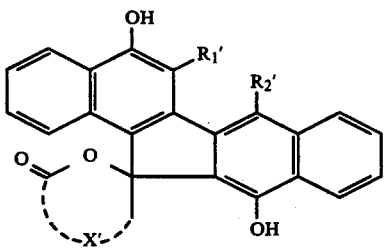

wherein R₁' and R₂' represent hydrogen or —CON(iPr)₂ provided at least one of R₁' and R₂' is —CON(iPr)₂.

18. A photographic film unit as defined in claim 1 wherein said pH-sensitive indicator dye contains the system represented by

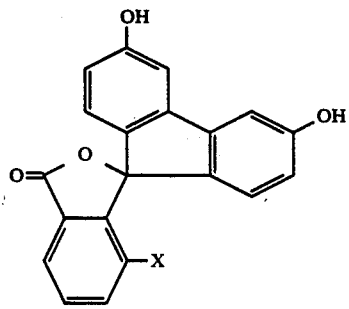

herein X is selected from carboxy or halide.

19. In a photographic process for forming a diffusion transfer image viewable as a reflection print which includes the steps of applying a layer of an aqueous alkaline processing composition comprising a light-reflecting pigment and at least one light-absorbing pH-sensitive optical filter agent between a negative component comprising an exposed silver halide emulsion carried on a support and a positive component comprising an image-receiving layer carried on a transparent support; said layer of processing composition being effective to develop said exposed silver halide emulsion and to form a visible image in said image-receiving layer and being effective to prevent transmission of light actinic to said silver halide emulsion during development thereof; and after a predetermined time, reducing the pH of said processing composition layer to a pH effective to decolorize said pH-sensitive optical filter agent; said pH reduction being effected by an acid-reacting layer disposed in at least one of said negative and positive components;

the improvement wherein at least one said light-absorbing pH-sensitive optical filter agent is a pH-sensitive bridged indicator dye of the formula

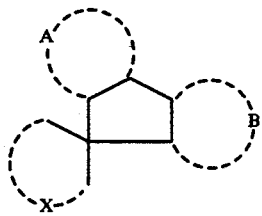

wherein A and B are selected from a first and second carbocyclic aryl radical, each possessing as a substituent an amino or hydroxy group positioned ortho or para to the meso carbon and meta to the bridging carbon, provided further that at least one of said A or B contains as said substituent a hydroxy group and, X represents the atoms necessary to complete a phenolate, carboxylate or sulfinate ester ring closing moiety; provided further that when X represents the atoms necessary to complete a phthalide or a sulfinate ester ring closing moiety, the phthalide or sulfinate ester moiety is not substituted in the 7'-position with a group which exerts a steric influence such that the lactone or sulfone, at a pH at or above its pKa, remains closed at room temperature.

20. A photographic process as defined in claim 19 wherein X represents a phthalide or naphthalide ring closing moiety.

21. A photographic process as defined in claim 19 wherein said A and said B are selected from said first and second carbocyclic aryl radicals each possessing as said substituent a hydroxy group.

22. A photographic process as defined in claim 19 wherein said pH-sensitive bridged indicator dye is represented by the formula

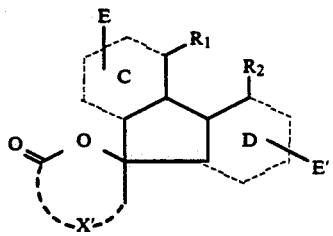

wherein C and D represent carbocyclic aryl groups; E and E' represent an amino or hydroxy group positioned either ortho or para to the meso carbon and meta to the bridging carbon, provided that at least one of E or E' is hydroxy; R₁ and R₂ represent bulky groups or hydrogen, provided at least one of R₁ and R₂ is a bulky group; and X' represents the atoms necessary to complete phthalide or naphthalide.

23. A photographic process as defined in claim 22 wherein said E and said E' are each hydroxy.

24. A photographic process as defined in claim 23 wherein one of said E and said E' is positioned ortho to the meso carbon and meta to the bridging carbon and the other of said E and said E' is positioned para to the meso carbon and meta to the bridging carbon.

25. A photographic process as defined in claim 24 further providing that said pH-sensitive bridged indicator dye shows a narrowing of the principal absorption bandwidth, a hypsochromic shift and an increase in molar absorptivity relative to the analogous pH-sensitive bridged indicator dye which has both hydroxy groups para to the meso carbon atom.

26. A photographic process as defined in claim 23 wherein both of said E and E' are positioned ortho to the meso carbon and meta to the bridging carbon.

27. A photographic process as defined in claim 22 wherein one of said R₁ or said R₂ is a bulky group and the other of said R₁ or R₂ is hydrogen.

28. A photographic process as defined in claim 27 wherein said bulky group is a substituted amide represented by

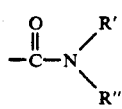

wherein R' and R" are branched alkyl groups.

29. A photographic process as defined in claim 27 wherein said bulky group is a substituted sulfonamide represented by

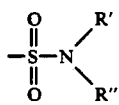

wherein R' and R" are branched alkyl groups.

30. A photographic process as defined in claim 19 wherein said processing composition additionally includes a viscosity-imparting reagent.

31. A photographic process as defined in claim 19 wherein said light-reflecting pigment is titanium dioxide.

32. A photographic process as defined in claim 19 wherein said processing composition includes a light-absorbing, pH-sensitive alkyl substituted phenanthrol/-carboxy-naphthol optical filter agent.

33. A photographic process as defined in claim 19 wherein said processing composition includes a light-absorbing indole phthalein optical filter agent.

34. A photographic process as defined in claim 22 wherein said pH-sensitive bridged indicator dye is represented by the formula

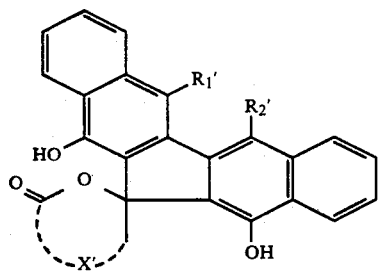

wherein $R_1'$ and $R_2'$ represent hydrogen or —CON(iPr)$_2$ provided at least one of $R_1'$ and $R_2'$ is —CON(iPr)$_2$.

35. A photographic process as defined in claim 22 wherein said pH-sensitive bridged indicator dye is represented by the formula

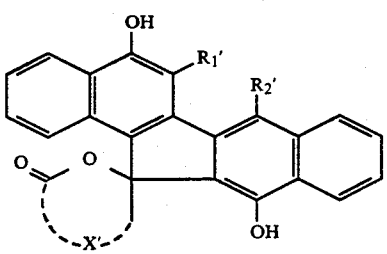

wherein $R_1'$ and $R_2'$ represent hydrogen or —CON(iPr)$_2$ provided at least one of $R_1'$ and $R_2'$ is —CON(iPr)$_2$.

36. A photographic process as defined in claim 19 wherein said pH-sensitive indicator dye contains the system represented by

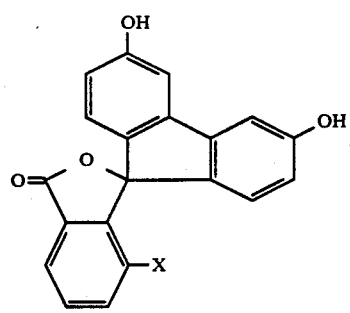

wherein X is selected from carboxy or halide.

37. A rupturable container for use in diffusion transfer film units adapted to provide transfer images viewable by reflected light, said rupturable container releasably holding an aqueous solution of alkali metal hydroxide, a light-reflecting pigment and at least one light-absorbing, pH-sensitive optical filter agent, at least one said optical filter being a pH-sensitive bridged indicator dye of the formula

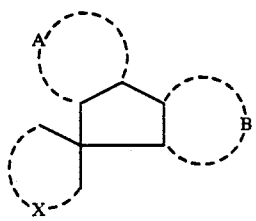

wherein A and B are selected from a first and second carbocyclic aryl radical each possessing as a substituent an amino or hydroxy group positioned ortho or para to the meso carbon and meta to the bridging carbon, provided further that at least one of said A and B contains as said substituent a hydroxy group and X represents the atoms necessary to complete a phenolate, carboxylate or sulfinate ester ring closing moiety, provided further that when X represents the atoms necessary to complete a phthalide or a sulfinate ester ring closing moiety, the phthalide or sulfinate ester moiety is not substituted in the 7'-position with a group which exerts a steric influence such that the lactone or sulfone, at a pH at or above its pKa, remains closed at room temperature.

38. A rupturable container releasably holding an aqueous alkaline processing composition as defined in claim 37 wherein X represents a phthalide or naphthalide ring closing moiety.

39. A rupturable container releasably holding an aqueous alkaline processing composition as defined in claim 37 wherein said A and said B are selected from said first and second carbocyclic aryl radicals each possessing as said substituent a hydroxy group.

40. A rupturable container releasably holding an aqueous alkaline processing composition as defined in claim 37 wherein said pH-sensitive bridged indicator dye is represented by the formula

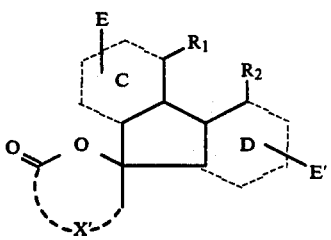

wherein C and C represent carbocyclic aryl group; E and E' represent an amino or hydroxy group positioned either ortho or para to the meso carbon and meta to the bridging carbon, provided that at least one of E or E' is hydroxy. $R_1$ and $R_2$ represent bulky groups or hydrogen, provided at least one of said R and $R_2$ is a bulky group; and X' represents the atoms necessary to complete phthalide or naphthalide.

41. A rupturable container releasably holding an aqueous alkaline processing composition as defined in claim 40 wherein said E and said E' are each hydroxy.

42. A rupturable container releasably holding an aqueous alkaline processing composition as defined in claim 41, wherein one of said E and said E' is positioned ortho to the meso carbon and meta to the bridging carbon and the other of said E and said E' is positioned para to the meso carbon and meta to the bridging carbon.

43. A rupturable container releasably holding an aqueous alkaline processing composition as defined in claim 42 further providing that said pH-sensitive bridged indicator dye shows a narrowing of the principal absorption bandwidth, a hypsochromic shift of λmax and an increase in molar absorptivity relative to the analogous pH-sensitive indicator dye which has both hydroxy groups para to the meso carbon.

44. A rupturable container releasably holding an aqueous alkaline processing composition as defined in claim 41 wherein both of said E and E' are positioned ortho to the meso carbon and meta to the bridging carbon.

45. A rupturable container releasably holding an aqueous alkaline processing composition as defined in claim 40 wherein one of said $R_1$ or $R_2$ is a bulky group and the other of said $R_1$ or $R_2$ is hydrogen.

46. A rupturable container releasably holding an aqueous alkaline processing composition as defined in claim 45 wherein said bulky group is a substituted amide represented by

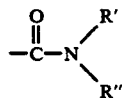

wherein R' and R" are branched alkyl groups.

47. A rupturable container releasably holding an aqueous alkaline processing composition as defined in claim 45 wherein said bulky group is a substituted sulfonamide represented by

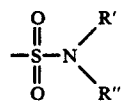

wherein R' and R" are branched alkyl groups.

48. A rupturable container releasably holding an aqueous alkaline processing composition as defined in claim 40 wherein said pH-sensitive bridged indicator dye is represented by the formula

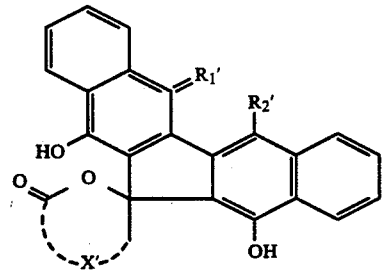

wherein $R_1'$ and $R_2'$ represent hydrogen or —CON(iPr)$_2$ provided at least one of $R_1'$ and $R_2'$ is —CON(iPr)$_2$.

49. A rupturable container releasably holding an aqueous alkaline processing composition as defined in claim 40 wherein said pH-sensitive bridged indicator dye is represented by the formula

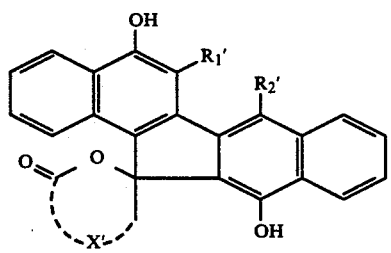

wherein $R_1'$ and $R_2'$ represent hydrogen or —CON(iPr)$_2$ provided at least one of $R_1'$ and $R_2'$ is —CON(iPr)$_2$.

50. A rupturable container releasably holding an aqueous alkaline processing composition as defined in claim 37 wherein said pH-sensitive indicator dye contains the system represented by

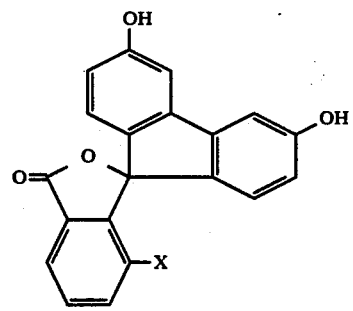

wherein X is selected from carboxy or halide.

51. A rupturable container releasably holding an aqueous alkaline processing composition as defined in claim 37 wherein said processing composition additionally includes a viscosity imparting reagent.

52. A rupturable container releasably holding an aqueous alkaline processing composition as defined in claim 37 wherein said light-reflecting pigment is titanium dioxide.

53. A rupturable container releasably holding an aqueous alkaline processing composition as defined in claim 37 wherein said processing composition includes a light-absorbing, pH-sensitive alkyl substituted phenanthrol/o-carboxynaphthol phthalein optical filter agent.

54. A rupturable container releasably holding an aqueous alkaline processing composition as defined in claim 37 wherein said processing composition includes a light-absorbing indole phthalein optical fiber agent.

* * * * *